US007595473B2

(12) United States Patent
Walt et al.

(10) Patent No.: US 7,595,473 B2
(45) Date of Patent: Sep. 29, 2009

(54) METHOD AND SYSTEM OF ARRAY IMAGING

(75) Inventors: David R. Walt, Boston, MA (US); Sandra Bencic-Nagale, Lowell, MA (US)

(73) Assignee: Tufts University, Medford, MA (US)

( * ) Notice: Subject to any disclaimer, the term of this patent is extended or adjusted under 35 U.S.C. 154(b) by 0 days.

(21) Appl. No.: 11/209,432

(22) Filed: Aug. 22, 2005

(65) Prior Publication Data

US 2007/0040095 A1    Feb. 22, 2007

(51) Int. Cl.
    *G01N 21/00* (2006.01)
(52) U.S. Cl. .............. 250/205; 250/216; 422/82.05; 422/91; 436/172
(58) Field of Classification Search ........... 250/237 R, 250/216, 205; 356/317, 318; 436/172; 422/82.05, 422/91
    See application file for complete search history.

(56) References Cited

U.S. PATENT DOCUMENTS

| | | | | |
|---|---|---|---|---|
| 4,691,110 A | * | 9/1987 | Nebe et al. | 250/458.1 |
| 5,512,490 A | * | 4/1996 | Walt et al. | 436/171 |
| 5,557,398 A | * | 9/1996 | Wechsler et al. | 356/318 |
| 5,784,152 A | | 7/1998 | Heffelfinger et al. | |
| 5,886,784 A | * | 3/1999 | Engelhardt | 356/326 |
| 6,379,969 B1 | * | 4/2002 | Mauze et al. | 436/68 |
| 6,545,758 B1 | * | 4/2003 | Sandstrom | 356/317 |
| 6,898,367 B2 | | 5/2005 | Berk et al. | |
| 2001/0028455 A1 | * | 10/2001 | Uhl | 356/317 |
| 2003/0002040 A1 | * | 1/2003 | MacAulay et al. | 356/317 |
| 2005/0157294 A1 | * | 7/2005 | Hopkins et al. | 356/328 |

OTHER PUBLICATIONS

Agayn, V., et al., "Fiber optic immunosensors based on continuous reagent delivery," *Immunomethods* 3(2):112-121 (1993).
Barnard, S., et al., "Chemical sensors based on controlled-release polymer systems," *Science* 251(4996):927-929 (1991).
Berrios, M., et al., "Antifading agents for confocal fluorescence microscopy," *Methods Enzymol.* 307:55-79 (1999).
Kermis, H., et al., "Dual excitation ratiometric fluorescent pH sensor for noninvasive bioprocess monitoring: development and application," *Biotechnol. Prog.* 18(5):1047-1053 (Sep.-Oct. 2002).
Krenik, K., et al., "Comparison of antifading agents used in immunofluorescence," *J. Immunol. Meth.* 117(1):91-97 (Feb. 1989).

(Continued)

*Primary Examiner*—Georgia Y Epps
(74) *Attorney, Agent, or Firm*—Wolf, Greenfield & Sacks, P.C.

(57) ABSTRACT

The present invention relates to a method and system of array imaging that extends or maximizes the longevity of the sensor array by minimizing the effects of photobleaching. The imaging system has a light source, a variable exposure aperture, and a variable filter system. The system extends the longevity of sensors by (1) using the variable exposure aperture to selectively expose sections of the sensor array containing representative numbers of each type of sensor, and/or (2) using the variable filter system to control the intensity of the excitation light, providing only the intensity required to induce the appropriate excitation and increasing that intensity over time as necessary to counteract the effects of photobleaching.

22 Claims, 4 Drawing Sheets

OTHER PUBLICATIONS

Shortreed, M., et al., "Lifetime enhancement of ultrasmall fluorescent liquid polymeric film based optodes by diffusion-induced self-recovery after photobleaching," *Anal. Chem.* 68(22):4015-4019 (Nov. 1996).

Song, A., et al., "High-performance fiber-optic pH microsensors for practical physiological measurements using a dual-emission sensitive dye," *Anal. Chem.* 69(5):863-867 (Mar. 1997).

Takayama, R., et al., "Pyroelectric Infrared array sensors made of c-axis oriented La-modified $PbTIO_3$ thin films," *Sens. Actuators A: Phys.* 22(1-3):508-512 (Jun. 1989).

Uttamlal, M., et al., "A fiber-optic carbon dioxide sensor for fermentation monitoring," *Bio/Technology* 13(6):597-601 (1995).

Xu, Z., et al., "A novel fiber-optic pH sensor Incorporating carboxy SNAFL-2 and fluorescent wavelength-ratiometric detection," *J. Biomed. Mater. Res.* 39(1):9-15 (Jan. 1998).

Yang, J., et al., "Porous shape persistent fluorescent polymer films: an approach to tnt sensory materials," *J. Am. Chem. Soc.* 120(21):5321-5322 (Jun. 1998).

International Search Report and Written Opinion for International Application No. PCT/US06/32608, mailed Jul. 23, 2008.

\* cited by examiner

METHOD AND SYSTEM OF ARRAY IMAGING

STATEMENT OF GOVERNMENT SPONSORED RESEARCH

The United States government may have certain rights in this invention pursuant to Contract No. F49620-01-1-0395, awarded by the United States Air Force, Office of Scientific Research.

CROSS-REFERENCE TO RELATED APPLICATION(S)

None.

FIELD OF THE INVENTION

The present invention relates to a method and system of array imaging. More specifically, the present invention relates to a method and system of array imaging that extends or maximizes the longevity of the sensor array by minimizing the effects of photobleaching.

BACKGROUND OF THE INVENTION

Fluorescence-based sensor longevity—the period during which sensors exhibit reproducible responses when exposed to an analyte—is limited. As the sensors are repeatedly exposed to light over time, they become less responsive, typically due to photobleaching. Certain sensor arrays retain responsiveness for an average of approximately one hundred responses or a total exposure time of less than 8 minutes.

The limited sensor life can be a limiting factor in the use of sensor arrays. In some cases, replacement of non-responsive sensors means having to replace the entire array or some portion thereof.

Sensor arrays for analyzing vapors (also referred to as "electronic noses"), for example, are limited by sensor life. Electronic noses detect changes in the response patterns of non-specific sensors exposed to vapors and categorize the vapors with the use of pattern recognition software. Ideally, electronic noses contain a diverse array of cross-reactive sensors. These arrays are typically composed of conducting polymer sensors or fluorescent sensors that produce patterns resulting from changes in the properties of the sensors over time. Such arrays use pattern recognition, storing the response patterns in a large database such that a wide range of vapors can subsequently be identified using the database. That is, during the training process, responses are collected from known vapors and those responses are then used to classify unknown vapors. A training database can be collected on one array and applied to multiple arrays over time, which eliminates the need for repetitive training. Ideally, a database should contain many replicate array responses from many vapors. One of the most important requirements for building large databases of vapor patterns is array longevity. In fact, for many such applications, only sensor arrays with long-term use capability and with less frequent replacement and servicing needs will be acceptable. It is understood that the more analytes that can be recognized, the more effective the array, thereby underscoring the need for an increased number of training replicates and inclusion of additional vapors in the training database. If an array degrades too fast, it will have to be replaced and the training will have to be repeated. Thus, the longevity of most fluorescent sensor arrays has typically been limited by the photobleaching rates of the fluorescent dyes attached to the individual beads.

Several approaches to overcome or compensate for photobleaching of fluorescent dyes and fluorescent sensors have focused on the dyes or sensing substrates. For example, certain ratiometric sensors have been introduced that are insensitive to photobleaching effects. See Kermis, H. R.; Kostov, Y.; Harms, P.; Rao, G. *Biotechnol. Progress* 2002, 18, 1047-1053; Song, A.; Parus, S.; Kopelman, R. *Anal. Chem.* 1997, 69, 863-867; and Xu, Z.; Rollins, A.; Alcala, R.; Marchant, R. E. *J. Biomed. Mater. Res.* 1998, 39, 9-15. Further, anti-fading agents have been added to dyes to chemically decrease the photobleaching rates of the dyes. See Berrios, M.; Conlon, K. A.; Colflesh, D. E. *Methods in Enzymology* 1999, 307, 55-79; Krenik, K. D.; Kephart, G. M.; Offord, K. P.; Dunnette, S. L.; Gleich, G. J. *Journal of Immunological Methods* 1989, 117, 91-97. Another approach involves increasing dye photostability by engineering fluorescent polymer molecules with structural properties that prevent $\pi$-stacking, thereby circumventing the fluorescence quenching caused by such $\pi$-stacking. See Yang, J.-S.; Swager, T. M. *J. Am. Chem. Soc.* 1998, 120, 5321-5322. Although somewhat successful, each of the above methods requires chemical modification of the indicator dyes or sensing substrates, or, in the case of ratiometric measurements, the use of different indicators altogether.

Other approaches have taken advantage of the physical properties of sensors to increase sensor longevity. One such approach involves incorporating fluorescent dye into a polymer matrix, resulting in a polymer layer containing freely diffusible dye molecules. See Shortreed, M., Monson, E., and R. Kopelman, *Anal. Chem.* 1996, 68, 4015-4019; Barnard, S. M. and D. R. Walt, "Chemical Sensors Based on Controlled-Release Polymer Systems," *Science,* 1991, 251 (4996): 927-9; Agayn, V. and D. R. Walt, "Fiber-Optic Immunosensors Based on Continuous Reagent Delivery," *Immunomethods,* 1993, 3(2): 112-21; and Uttamlal, M. and D. R. Walt, "A Fiber-Optic Carbon Dioxide Sensor for Fermentation Monitoring," *Bio/Technology,* 1995, 13 (6): 597-601. In use, a small portion of the layer is selectively illuminated and as the dye molecules are photobleached, they are replaced with new dye molecules that diffuse from a reservoir into the illuminated polymer film area, thereby increasing the number of sensor measurements possible. Another approach involving an IR detector focused on sectioning the array with an optical slit. See Takayama, R.; Tomita, Y.; Asayama, J.; Nomura, K., and H. Ogawa, *Sens. Actuators A: Physical* 1990, A22, 508-512. That is, the optical slit served to selectively illuminate individual IR detectors in a microarray and the response of each detector was monitored during and after the illumination.

However, the Shortreed et al. and Walt et al. methods described above are limited to devices using the polymer layer containing diffusible molecules. Thus, the methods cannot be implemented using any known non-diffusible sensors. Further, the Takayama et al. optical slit described above is used in conjunction with an array comprised of only one type of sensor.

There is a need in the art for a method and system of array imaging that extends or maximizes the longevity of the sensor array by minimizing the effects of photobleaching.

BRIEF SUMMARY OF THE INVENTION

The present invention, in one embodiment, is a method of detecting the presence of at least one target analyte in at least a first and a second sample. The method includes contacting the first sample with a sensor array comprising a plurality of sensor element types and a plurality of sensor elements of each sensor element type. The method further includes illuminating at least a first section of the sensor array with a first intensity and collecting a first set of data. In addition, the method includes contacting the second sample with the sensor array and illuminating at least a second section of the sensor array with a second intensity and collecting a second set of data. Further, the method includes determining the presence or absence of the target analytes. In one aspect of this embodiment, the first and second sections are the same, or alternatively they are different. The second intensity, according to one embodiment, is greater than the first intensity, or, alternatively, it is substantially similar to the first intensity. Illuminating the sensor array can include illuminating the sensor array through a variable exposure aperture, according to one embodiment. The variable exposure aperture can be positionable. It can also be a slit, including a rectangular-shaped slit.

The present invention, in another embodiment, is array imaging system having a light source, an array receiving component, a variable exposure aperture, and a variable filter system. The variable exposure aperture is disposed between the light source and the array receiving component, and the variable filter system is disposed between the light source and the array receiving component. The system can also, in one embodiment, have a magnification lens disposed between the light source and the array receiving component. In addition, the system can also have an array detector associated with the magnification lens. The variable filter system, according to one aspect of the invention, is programmable to decrease in optical density over time. In one embodiment, the variable filter system includes a set of filters disposed between the light source and the array receiving component, the set of filters being programmed to provide decreasing optical density. The set of filters can have filters of varying optical densities. In one aspect of the invention, the variable exposure aperture is a positionable aperture configured to operate with the light source to control an area of exposure. In a further embodiment, the variable exposure aperture has a slit configured to allow light to pass through from the light source to the sensor array.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

The present invention relates to a method and system of array imaging that extends or maximizes the longevity of the sensor array by minimizing the effects of photobleaching. The imaging system has a light source, a variable exposure aperture, and a variable filter system. In use, the system extends the longevity of sensors through an adaptive light exposure system by (1) using the variable exposure aperture to selectively expose sections of the sensor array containing representative numbers of each type of sensor, and/or (2) using the variable filter system to control the intensity of the excitation light, providing only the intensity required to induce the appropriate excitation and increasing that intensity over time as necessary to counteract the effects of photobleaching. The reduction in light intensity and selective illumination of sections of the array—rather than the entire array—can result in increased sensor longevity and shorter analysis time (because the limited exposure translates into fewer sensors being used for data analysis).

Figure 1:
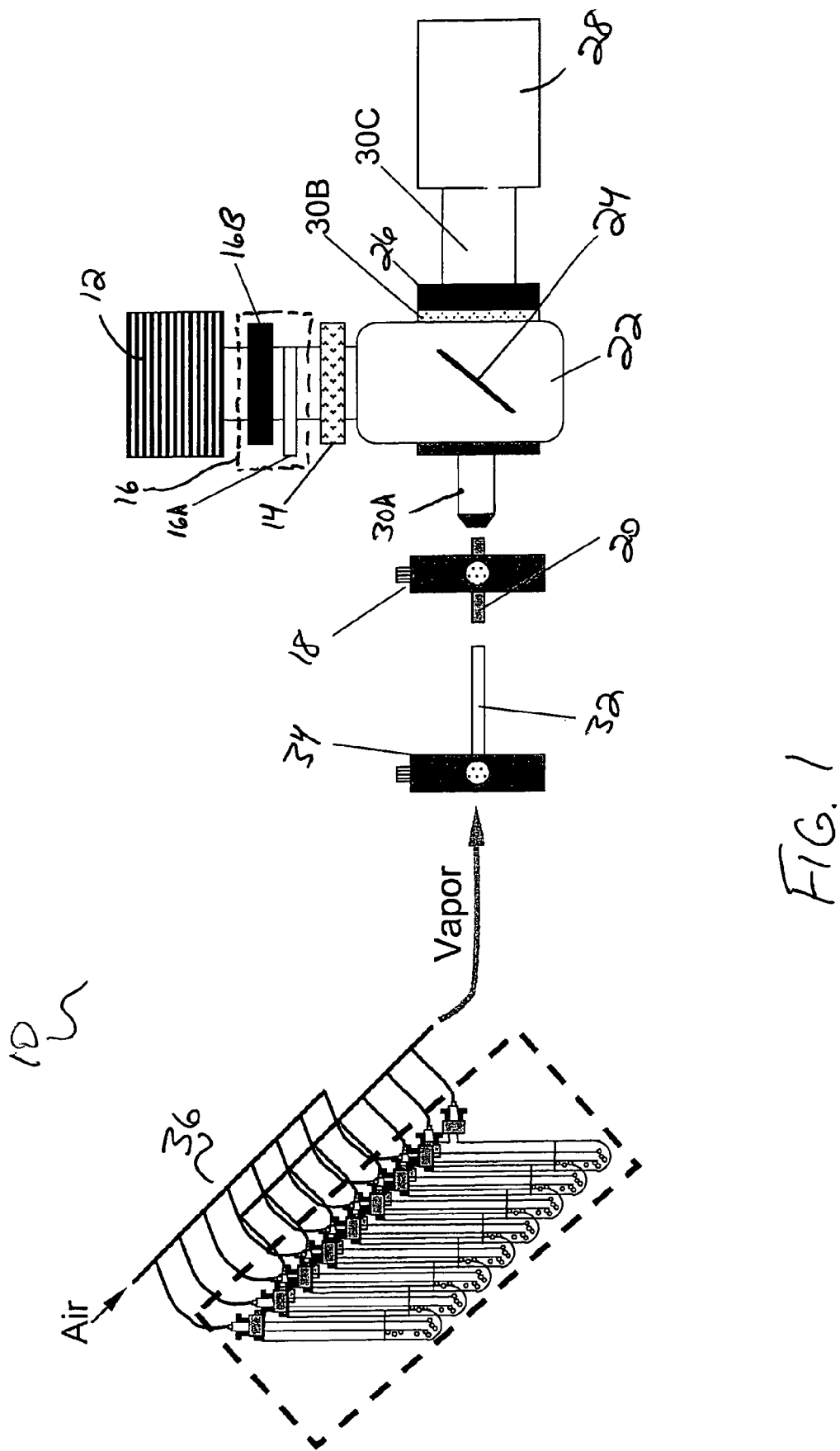
FIG. 1 is a schematic drawing showing an array imaging system, according to one embodiment of the present invention.

FIG. 1 depicts an array imaging system 10 according to one embodiment of the present invention. The system 10 has an excitation light source 12, a variable exposure aperture 14, a variable excitation filter system 16, and an array receiving component 18, which is configured to receive the sensor array 20. The exposure aperture 14 and the filter system 16 are positioned between the light source 12 and the sensor array 20. The system also includes a dichroic housing 22 containing a dichroic mirror 24, an emission filter system 26, an array detector 28, lens 30A, lens 30B, and lens 30C. The dichroic housing 22, the dichroic mirror 24, and the emission filter system 26 are positioned between the sensor array 20 and the array detector 28. The lens 30A is positioned between the sensor array 20 and the dichroic housing 22, while the lenses 30B and 30C are positioned between the dichroic mirror 24 and the array detector 28. More specifically, according to one embodiment, lens 30B is positioned between the dichroic housing 22 and the emission filter wheel 26, and lens 30C is positioned between the emission filter wheel 26 and the array detector 28. Alternatively, the lenses are positioned in any known fashion.

In one aspect of the invention, the system 10 is any known fluorescence microscope to which is added a variable exposure aperture 14 and a variable excitation filter system 16. For example, the fluorescence microscope can be the BX Olympus horizontal microscope, available from Olympus. In a further embodiment, the system 10 includes imaging software that can control certain components of the system 10 automatically. For example, the imaging software in one aspect of the invention can control at least portions of the light source 12, the variable exposure aperture 14 the filter systems 16, the emission filter system 26, and the array detector 28. In one example, the imaging software is the IPLab imaging software available from Scanalytics in Fairfax, Va. Alternatively, the imaging software is any known software for controlling components such as those listed above.

The excitation light source 12 can be any known light source for use in a fluorescence microscope. In one example, the excitation light source is a 75 Watt Xenon excitation source, available from Ludl in Hawthorne, N.Y.

The variable exposure aperture 14 (also referred to herein as a "slit") controls the size and shape of the field of excitation light, thereby controlling the size and shape of the area of the sensor array that is exposed by the light source 12. In one aspect of the present invention, the slit 14 is an adjustable rectangular field stop 14, which is a rectangular diaphragm having adjustable portions that can be variably positioned to create a rectangular or square excitation light field of any size to an accuracy of within tenths of microns, limited only by the total size of the field. In one alternative, the slit 14 is a diaphragm that can be variably positioned to create a circular excitation light field of any size to an accuracy of within tenths of microns. Thus, the adjustable rectangular field stop 14 provides for illuminating any section of the sensor array 20 with an illumination field of any predetermined size and any shape that can be created by any known rectangular field stop or diaphragm. According to one embodiment, the field stop 14 forms an optical slit that creates an exposed area on the array with dimensions of about 60 µm by about 300 µm. Alternatively, the size of the slit can vary from about 100 µm×100 µm (which, in one embodiment, creates an exposed area on the array of about 5 µm×5 µm at 20× magnification) to about 7 mm×7 mm.

In one example, the variable exposure aperture 14 is a rectangular field stop available from Olympus. Alternatively, the variable exposure aperture 14 can be any known diaphragm, field stop, or similar device for controlling the size and shape of the field of excitation light, and thus the field can have any one of a variety of geometries, such as square, rectangular, parallelogram, and circular.

While the variable exposure aperture 14 as depicted in FIG. 1 is positioned between the excitation light source 12 and the dichroic mirror 24, the aperture 14 can alternatively be positioned in any focal point between the light source 12 and the sensor array 20.

As shown in FIG. 1, the variable excitation filter system 16 according to one embodiment has two components: (1) a single neutral density ("ND") filter 16A, and (2) a variable filter component 16B. In one aspect of the invention, the filter system 16 is an automated dual excitation filter wheel 16 that accommodates both variable filters 16A and 16B. Such a wheel 16 allows for providing any combination of the filters 16A and 16B. The single ND filter 16A in one aspect of the invention has an optical density of 1.0. Alternatively, the ND filter 16A can have any known optical density. In a further alternative, the system 16 has only a variable filter component 16B.

The variable filter component 16B, according to one embodiment, is a filter wheel 16B that provides 10 filters having different optical densities, any of which can be used to provide the desired reduction in illumination intensity. The wheel 16B can also be set such that no filter is placed in the path of the illumination. Alternatively, the filter wheel 16B can have any known number of filters. According to one embodiment, the wheel 16B has five filters with optical densities of 0.2, 0.4, 0.6, 0.8, and 1.0. Using the wheel 16B with those filters in combination with the single ND filter 16A results in six different ND settings with the following OD values: 2.0, 1.8, 1.6, 1.4, 1.2, and 1.0, corresponding to 1%, 1.6%, 2.5%, 4%, 6.3%, and 10% transmittance, respectively.

In one aspect of the present invention, the variable filter system 16 provides filters providing a range of optical densities from about 0 to about 4. Alternatively, the system 16 provides filters providing a range of optical densities from about 1 to about 2.

In one aspect of the invention, the filters of the variable filter system 16 differ in optical density in increments of 0.2

(that is, each filter differs in optical density by 0.2 from each of the filters that has a greater and a lesser optical density). Alternatively, the variable filter system 16 has filters that differ in optical density in increments of 0.1. In a further alternative, the filters of the system 16 are provided in increments of less than 0.1.

According to one embodiment, the filter wheel is an automated filter wheel. One example of an automated filter wheel that can be used in the present invention is the LEP filter wheel with a MAC 5000 controller system, available from Ludl Electronic Products Ltd. in Hawthorne, N.Y. In an alternative embodiment, the variable excitation filter system 16 can include any known component configured to allow for adjustable filter settings, such as, for example, a filter slider or any similar device, thereby providing for filters having any known optical density. In one aspect of the invention, the filters positioned in the filter wheel 16B are absorptive neutral density ("ND") filters available from Newport Optics in Irvine, Calif. Alternatively, the filters are any known filters for use in a fluorescence microscope.

The array receiving component 18 as depicted in FIG. 1 is positionable with respect to the rest of the system 10. In one embodiment, the component 18 is positionable in the x-y direction. Alternatively, the component 18 is positionable in the z direction or in both the x-y direction and the z direction.

The sensor array 20 of the present invention is an array having at least a first substrate with a surface comprising individual sites. By "array" herein is meant a plurality of candidate agents in an array format; the size of the array depending on the composition and end use of the array. Arrays containing from about 2 different active agents to many millions can be made, with very large arrays, including very large fiber optic arrays, being possible. Generally, the array will comprise from two to as many as a billion or more, depending on the size of the beads and the substrate, as well as the end use of the array, thus very high density, high density, moderate density, low density and very low density arrays may be made. Ranges for very high density arrays, according to one embodiment, are from about 10,000,000 to about 2,000,000,000 (all numbers are per square cm), while alternatively the ranges are from about 100,000,000 to about 1,000,000,000. High density arrays range about 100,000 to about 10,000,000, while alternatively, they range from about 1,000,000 to about 5,000,000. Moderate density arrays range from about 10,000 to about 100,000, and alternatively from about 20,000 to about 50,000. Low density arrays are generally less than 10,000. In one embodiment, the low density arrays range from about 1,000 to about 5,000. Very low density arrays are less than 1,000. According to one embodiment, the very low density arrays range from about 10 to about 1000, and alternatively range from about 100 to about 500. In some embodiments, the compositions of the invention may not be in array format; that is, for some embodiments, compositions comprising a single active agent may be made as well. In addition, in some arrays, multiple substrates may be used, either of different or identical compositions. Thus for example, large arrays may comprise a plurality of smaller substrates.

In addition, one advantage of the present compositions is that particularly through the use of fiber optic technology, extremely high density arrays can be made. Thus for example, because beads of 200 μm or less (with beads of 200 nm possible) can be used, and very small fibers are known, it is possible to have as many as 40,000 or more (in some instances, 1 million) different fibers and beads in a 1 $mm^2$ fiber optic bundle, with densities of greater than 15,000,000 individual beads and fibers (again, in some instances as many as 25-50 million) per 0.5 $cm^2$ obtainable.

Suitable arrays include, but are not limited to, U.S. Pat. Nos. 6,023,540, 6,266,459, 6,327,410, 6,429,027, 6,858,394, and 6,859,570, U.S. Published Applications 2005/0130188 and 2003/0027126, U.S. application Ser. No. 10/005,201, filed on Dec. 4, 2001, and Published PCT Application WO 00/60332, all of which are incorporated herein by reference in their entirety.

By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., Tetrahedron, 49(10):1925 (1993) and references therein; Letsinger, *J. Org. Chem.*, 35:3800 (1970); Sprinzl, et al., *Eur. J. Biochem.*, 81:579 (1977); Letsinger, et al., *Nucl. Acids Res.*, 14:3487 (1986); Sawai, et al., *Chem. Lett.*, 805 (1984), Letsinger, et al., *J. Am. Chem. Soc.*, 110:4470 (1988); and Pauwels, et al., *Chemica Scripta*, 26:141 (1986)), phosphorothioate (Mag, et al., *Nucleic Acids Res.*, 19:1437 (1991); and U.S. Pat. No. 5,644, 048), phosphorodithioate (Briu, et al., *J. Am. Chem. Soc.*, 111:2321 (1989)), O-methylphophoroamidite linkages (see Eckstein, Oligonucleotides and Analogues: A Practical Approach, Oxford University Press), and peptide nucleic acid backbones and linkages (see Egholm, *J. Am. Chem. Soc.*, 114:1895 (1992); Meier, et al., *Chem. Int. Ed. Eng.*, 31:1008 (1992); Nielsen, *Nature*, 365:566 (1993); Carlsson, et al., *Nature*, 380:207 (1996), all of which are incorporated by reference)). Other analog nucleic acids include those with positive backbones (Denpcy, et al., *Proc. Natl. Acad. Sci. USA*, 92:6097 (1995)); non-ionic backbones (U.S. Pat. Nos. 5,386,023; 5,637,684; 5,602,240; 5,216,141; and 4,469,863; Kiedrowshi, et al., *Angew. Chem. Intl. Ed. English*, 30:423 (1991); Letsinger, et al., *J. Am. Chem. Soc.*, 110:4470 (1988); Letsinger, et al., Nucleosides & Nucleotides, 13:1597 (1994); Chapters 2 and 3, ASC Symposium Series 580, "Carbohydrate Modifications in Antisense Research", Ed. Y. S. Sanghui and P. Dan Cook; Mesmaeker, et al., *Bioorganic & Medicinal Chem. Lett.*, 4:395 (1994); Jeffs, et al., *J. Biomolecular NMR*, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al., *Chem. Soc. Rev.*, (1995) pp. 169-176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. According to one exemplary embodiment, an analog nucleic acid useful in the present invention is PNA. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthanine, hypoxanthanine, isocytosine, isoguanine, and base analogs such as nitropyrrole and nitroindole, etc.

By "substrate" or "solid support" or other grammatical equivalents herein is meant any material that can be modified to contain discrete individual sites appropriate for the attachment or association of beads and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses, plastics, optical fiber bundles, and a variety of other polymers. In general, the substrates allow optical detection and do not themselves appreciably fluoresce.

Generally the substrate is flat (planar), although as will be appreciated by those in the art, other configurations of substrates may be used as well; for example, three dimensional configurations can be used, for example by embedding the beads in a porous block of plastic that allows sample access to the beads and using a confocal microscope for detection. Similarly, the beads may be placed on the inside surface of a tube, for flow-through sample analysis to minimize sample volume. According to one embodiment, substrates used with the present invention are optical fiber bundles as discussed below, or, alternatively, flat planar substrates such as glass, polystyrene and other plastics and acrylics.

In one embodiment, the substrate is an optical fiber bundle or array, as is generally described in U.S. Ser. Nos. 08/944,850 and 08/519,062, PCT US98/05025, and PCT US98/09163, all of which are expressly incorporated herein by reference. Certain embodiments utilize preformed unitary fiber optic arrays. By "preformed unitary fiber optic array" herein is meant an array of discrete individual fiber optic strands that are co-axially disposed and joined along their lengths. The fiber strands are generally individually clad. However, one thing that distinguished a preformed unitary array from other fiber optic formats is that the fibers are not individually physically manipulatable; that is, one strand generally cannot be physically separated at any point along its length from another fiber strand.

Generally, the array of array compositions of the invention can be configured in several ways; see for example U.S. Ser. No. 09/473,904, hereby expressly incorporated by reference. In one aspect of the invention, a first substrate comprising a plurality of assay locations (sometimes also referred to herein as "assay wells"), such as a microtiter plate, is configured such that each assay location contains an individual array. That is, the assay location and the array location are the same. For example, the plastic material of the microtiter plate can be formed to contain a plurality of "bead wells" in the bottom of each of the assay wells. Beads containing the active agent of the invention can then be loaded into the bead wells in each assay location as is more fully described below.

In one embodiment in which the substrate has a plurality of assay wells with a plurality of bead wells in the bottom of each assay well, the bead wells are discrete individual sites appropriate for the attachment or association of beads formed on the inner surface of each assay well. Alternatively, the bead wells are discrete individual sites formed on individual fibers of a fiber optic bundle embedded in each assay well. For example, fiber optic bundles can be embedded in the microtiter wells. In a further alternative, the bead wells are formed on the flat surface of the substrate, either for example by etching or drilling wells, or by embedding fiber optic bundles in the slide (for example this can be done by embedding fiber optic bundles in a block of glass or plastic (or other materials) and then "slicing" planar sections. In these embodiments, an additional substrate layer is placed on top of the substrate (on the same side as the bead wells), wherein the additional substrate layer has holes that correspond to the locations of the bead wells. As such, the holes in the additional substrate layer create assay wells in which bead wells formed in the flat surface of the substrate are located within each of the assay wells. For example, a silicon or rubber layer or gasket can be applied, or a second sheet of plastic or glass. In a further embodiment, the wells are contained on a flat surface and the assay locations are created not by the use of a second physical layer, but rather by the use of chemical functionality. For example, the addition of hydrophobic solvent in a pattern allows for the separation of hydrophilic samples; thus, for example, a "grid" of hydrophobic material can be applied to fluidically separate the array locations. Alternatively, other physical methodologies may be used, such as etching.

In one aspect of the invention, the substrate is a microtiter plate. Alternatively, the substrate is a microscope slide. In a further alternative, the substrate is any known substantially planar substrate.

At least one surface of the substrate is modified to contain discrete, individual sites for later association of microspheres. These sites may comprise physically altered sites, i.e. physical configurations such as wells or small depressions in the substrate that can retain the beads, such that a microsphere can rest in the well, or the use of other forces (magnetic or compressive), or chemically altered or active sites, such as chemically functionalized sites, electrostatically altered sites, hydrophobically/hydrophilically functionalized sites, spots of adhesive, etc.

The sites may be a pattern, i.e. a regular design or configuration, or randomly distributed. One embodiment utilizes a regular pattern of sites such that the sites may be addressed in the X-Y coordinate plane. "Pattern" in this sense includes a repeating unit cell, preferably one that allows a high density of beads on the substrate. However, it should be noted that these sites may not be discrete sites. That is, it is possible to use a uniform surface of adhesive or chemical functionalities, for example, that allows the association of beads at any position. That is, the surface of the substrate is modified to allow association of the microspheres at individual sites, whether or not those sites are contiguous or non-contiguous with other sites. Thus, the surface of the substrate may be modified such that discrete sites are formed that can only have a single associated bead, or alternatively, the surface of the substrate is modified and beads may go down anywhere, but they end up at discrete sites.

In one aspect of the present invention, the surface of the substrate is modified to contain wells, i.e. depressions in the surface of the substrate. This may be done as is generally known in the art using a variety of techniques, including, but not limited to, photolithography, stamping techniques, molding techniques and microetching techniques. As will be appreciated by those in the art, the technique used will depend on the composition and shape of the substrate.

In one embodiment, physical alterations are made in a surface of the substrate to produce the sites. According to one aspect of the present invention, the substrate is a fiber optic bundle and the surface of the substrate is a terminal end of the fiber bundle, as is generally described in Ser. Nos. 08/818,199 and 09/151,877, both of which are hereby expressly incorporated by reference. In this embodiment, wells are made in a terminal or distal end of a fiber optic bundle comprising individual fibers. In this embodiment, the cores of the individual fibers are etched, with respect to the cladding, such that small wells or depressions are formed at one end of the fibers. The required depth of the wells will depend on the size of the beads to be added to the wells.

Generally in this embodiment, the microspheres are non-covalently associated in the wells, although the wells may additionally be chemically functionalized as is generally described below, cross-linking agents may be used, or a physical barrier may be used, i.e. a film or membrane over the beads.

In accordance with one embodiment, the surface of the substrate is modified to contain chemically modified sites, that can be used to associate, either covalently or non-covalently, the microspheres of the invention to the discrete sites or locations on the substrate. "Chemically modified sites" in this context includes, but is not limited to, the addition of a pattern of chemical functional groups including amino groups, carboxy groups, oxo groups and thiol groups, that can be used to covalently attach microspheres, which generally also contain corresponding reactive functional groups; the addition of a pattern of adhesive that can be used to bind the microspheres (either by prior chemical functionalization for the addition of the adhesive or direct addition of the adhesive); the addition of a pattern of charged groups (similar to the chemical functionalities) for the electrostatic association of the microspheres, i.e. when the microspheres comprise charged groups opposite to the sites; the addition of a pattern of chemical functional groups that renders the sites differentially hydrophobic or hydrophilic, such that the addition of similarly hydrophobic or hydrophilic microspheres under suitable experimental conditions will result in association of the microspheres to the sites on the basis of hydroaffinity. For example, the use of hydrophobic sites with hydrophobic beads, in an aqueous system, drives the association of the beads preferentially onto the sites. As outlined above, "pattern" in this sense includes the use of a uniform treatment of the surface to allow association of the beads at discrete sites, as well as treatment of the surface resulting in discrete sites. As will be appreciated by those in the art, this may be accomplished in a variety of ways.

By "microspheres" or "beads" or "particles" or grammatical equivalents herein is meant small discrete particles. The composition of the beads will vary, depending on the class of active agent and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon may all be used. "*Microsphere Detection Guide*" from Bangs Laboratories, Fishers Ind. is a helpful guide.

The beads need not be spherical; irregular particles may be used. In addition, the beads may be porous, thus increasing the surface area of the bead available for either active agent attachment or IBL attachment. The bead sizes range from nanometers, i.e. 100 nm, to millimeters, i.e. 1 mm, with beads from about 0.2 micron to about 200 microns, and alternatively from about 0.5 to about 5 micron, although in some embodiments smaller beads may be used.

It should be noted that a key component of the invention is the use of a substrate/bead pairing that allows the association or attachment of the beads at discrete sites on the surface of the substrate, such that the beads do not move during the course of the assay.

Each microsphere comprises an active agent, although as will be appreciated by those in the art, there may be some microspheres which do not contain an active agent, depending on the synthetic methods. By "candidate active agent" or "active agent" or "chemical functionality" or "binding ligand" as used herein describes any molecule which can be attached to the microspheres of the invention and is generally used for the detection of target analytes, including both biological and chemical target analytes. According to one embodiment, the active agent is a bioactive agent such as a protein, oligopeptide, small organic molecule, coordination complex, polysaccharide, polynucleotide, etc. Alternatively, the active agent is a chemically active agent. It should be understood that the compositions of the invention have two primary uses. In one embodiment, as is more fully outlined below, the compositions are used to detect the presence of a particular target analyte; for example, the presence or absence of a particular nucleotide sequence or a particular protein, such as an enzyme, an antibody or an antigen. For example, the compositions can be used to detect vapor phase analytes (e.g. volatile organic compounds, explosives, chemical warfare agents, bacteria headspace, food aromas, etc.). Alternatively, the compositions are used to screen active agents, i.e. drug candidates, for binding to a particular target analyte.

Bioactive agents encompass numerous chemical classes, though typically they are organic molecules, preferably small organic compounds having a molecular weight of more than 100 and less than about 2,500 Daltons. Bioactive agents comprise functional groups necessary for structural interaction with proteins, particularly hydrogen bonding, and typically include at least an amine, carbonyl, hydroxyl or carboxyl group, preferably at least two of the functional chemical groups. The bioactive agents often comprise cyclical carbon or heterocyclic structures and/or aromatic or polyaromatic structures substituted with one or more of the above functional groups. Bioactive agents are also found among biomolecules including peptides, nucleic acids, saccharides, fatty acids, steroids, purines, pyrimidines, derivatives, structural analogs or combinations thereof. In one embodiment, the bioactive agents are nucleic acids and proteins.

Active agents can be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification and/or amidification to produce structural analogs.

In one aspect of the invention, the bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. The side chains may be in either the (R) or the (S) configuration. In this embodiment, the amino acids are in the (S) or L-configuration. If non-naturally occurring side chains are used, non-amino acid substituents may be used, for example to prevent or retard in vivo degradations.

In one embodiment, the bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. In one embodiment, the bioactive agents are libraries of bacterial, fungal, viral, and mammalian proteins, including, according to one embodiment, human proteins.

The bioactive agents, in one aspect of the present invention, are peptides of from about 5 to about 30 amino acids, or alternatively are about 5 to about 20 amino acids, and in a further alternative are about 7 to about 15 amino acids. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized bioactive proteinaceous agents.

A library of active agents are used, according to one embodiment. The library should provide a sufficiently structurally diverse population of active agents to effect a probabilistically sufficient range of binding to target analytes. Accordingly, an interaction library must be large enough so that at least one of its members will have a structure that gives it affinity for the target analyte. Although it is difficult to gauge the required absolute size of an interaction library, nature provides a hint with the immune response: a diversity of $10^7$-$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. Thus, in one aspect of the invention, at least $10^6$, alternatively at least $10^7$, in a further alternative at least $10^8$, and in yet another alternative at least $10^9$ different active agents are simultaneously analyzed in the subject methods. According to one embodiment, the methods maximize library size and diversity.

In one embodiment, the library is fully randomized, with no sequence preferences or constants at any position. Alternatively, the library is biased. That is, some positions within the sequence are either held constant, or are selected from a limited number of possibilities. For example, in one aspect of the invention, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In one aspect of the present invention, the bioactive agents are nucleic acids (generally called "probe nucleic acids" or "candidate probes" herein). By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., Tetrahedron, 49(10):1925 (1993) and references therein; Letsinger, J. Org. Chem., 35:3800 (1970); Sprinzl, et al., Eur. J. Biochem., 81:579 (1977); Letsinger, et al., Nucl. Acids Res., 14:3487 (1986); Sawai, et al., Chem. Lett., 805 (1984), Letsinger, et al., J. Am. Chem. Soc., 110:4470 (1988); and Pauwels, et al., Chemica Scripta, 26:141 (1986)), phosphorothioate (Mag, et al., Nucleic Acids Res., 19:1437 (1991); and U.S. Pat. No. 5,644,048), phosphorodithioate (Briu, et al., J. Am. Chem. Soc., 111:2321 (1989)), O-methylphophoroamidite linkages (see Eckstein, Oligonucleotides and Analogues: A Practical Approach, Oxford University Press), and peptide nucleic acid backbones and linkages (see Egholm, J. Am. Chem. Soc., 114:1895 (1992); Meier, et al., Chem. Int. Ed. Engl., 31:1008 (1992); Nielsen, Nature, 365: 566 (1993); Carlsson, et al., Nature, 380:207 (1996), all of which are incorporated by reference)). Other analog nucleic acids include those with positive backbones (Denpcy, et al., Proc. Natl. Acad. Sci. USA, 92:6097 (1995)); non-ionic backbones (U.S. Pat. Nos. 5,386,023; 5,637,684; 5,602,240; 5,216,141; and 4,469,863; Kiedrowshi, et al., Angew. Chem. Intl. Ed. English, 30:423 (1991); Letsinger, et al., J. Am. Chem. Soc., 110:4470 (1988); Letsinger, et al., Nucleosides & Nucleotides, 13:1597 (1994); Chapters 2 and 3, ASC Symposium Series 580, "Carbohydrate Modifications in Antisense Research", Ed. Y. S. Sanghui and P. Dan Cook; Mesmaeker, et al., Bioorganic & Medicinal Chem. Lett., 4:395 (1994); Jeffs, et al., J. Biomolecular NMR, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al., Chem. Soc. Rev., (1995) pp. 169-176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. For example, PNA is a nucleic acid analog in one embodiment of the present invention. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthanine, hypoxanthanine, isocytosine, isoguanine, and base analogs such as nitropyrrole and nitroindole, etc.

In one embodiment, the bioactive agents are libraries of clonal nucleic acids, including DNA and RNA. In this embodiment, individual nucleic acids are prepared, generally using conventional methods (including, but not limited to, propagation in plasmid or phage vectors, amplification techniques including PCR, etc.). The nucleic acids are preferably arrayed in some format, such as a microtiter plate format, and beads added for attachment of the libraries.

Attachment of the clonal libraries (or any of the nucleic acids outlined herein) may be done in a variety of ways, as will be appreciated by those in the art, including, but not limited to, chemical or affinity capture (for example, including the incorporation of derivatized nucleotides such as AminoLink or biotinylated nucleotides that can then be used to attach the nucleic acid to a surface, as well as affinity capture by hybridization), cross-linking, and electrostatic attachment, etc.

By "labeled" herein is meant that a compound has at least one element, isotope or chemical compound attached to enable the detection of the compound. In general, labels fall into three classes: a) isotopic labels, which may be radioactive or heavy isotopes; b) magnetic, electrical, thermal; and c) colored or luminescent dyes; although labels include enzymes and particles such as magnetic particles as well. According to one embodiment, labels used with the present invention include luminescent labels. Suitable labels include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue™, Texas Red, FITC, PE, cy3, cy5 and others described in the 6th Edition of the Molecular Probes Handbook by Richard P. Haugland, hereby expressly incorporated by reference.

The sensor array 20, in accordance with one aspect of the present invention, is a microbead sensor array 20. In one embodiment, the use of a substrate/bead pairing allows the association or attachment of the beads at discrete sites on the surface of the substrate, such that the beads do not move during the course of the assay.

In certain embodiments in which the array 20 is a bead sensor array 20, the present invention includes a population of microspheres. By "population" herein is meant a plurality of sensors as outlined above for arrays. Where the array 20 is a bead sensor array, the population is a plurality of microspheres.

Within the population are separate subpopulations (also referred to herein as "types," "groups," or "subsets"), which can be a single sensor or multiple identical sensors. That is, in some embodiments, as is more fully outlined below, the array may contain only a single sensor for each active agent; while other embodiments utilize a plurality of sensors of each type.

In embodiments in which the sensor array is a microsphere sensor array, the subpopulations which are characterized by the active agent attached to the microsphere and can be a single microsphere or multiple identical microspheres. According to one aspect of the invention, the use of more than one subpopulation, wherein each subpopulation comprises a plurality of microspheres containing the same active agent, provides a redundancy that is built into the system. That is, providing subpopulations or subgroups of microspheres having multiple microspheres containing the same active agent ensures that numerous microsphere replicates exist within any array of the present invention.

The array 20 according to one embodiment has a population of 24,000 microbead sensors randomly distributed across the array in wells etched on one end of optical imaging fibers. Each sensor falls into one of four sensor subpopulations or types (also referred to as "groups" or "subsets") such that there are statistically approximately 6,000 replicates of each sensor type. In the present invention, a substantial number of replicates ensures that exposure of selected portions of an array results in exposure of a statistically significant number of each type of sensor. Alternatively, the array 20 has from about 20 to about 50,000 microbead sensors and from about 4 to about 15 sensor types. In a further alternative, the array 20 has any known number of microbead sensors and any known number of sensor types for identifying target analytes in an array imaging system. The microbead sensors that can be used in the present invention include, but are not limited to, Alltech, Chirex, Sel, or Snafl bead sensors.

As is understood in the art, the microbead/optical imaging fiber array 20 is typically positioned such that the excitation light from the light source 12 strikes the proximal faces of the fibers in the array 20 and passes through the fibers to the microbead sensors positioned on the distal face of the fibers. According to certain embodiments of the present invention, the variable exposure aperture 14 creates an excitation light field that strikes only a small portion of the proximal fiber faces such that when the light passes through those particular fibers, only a corresponding small portion of the microbead sensors positioned on the distal face of those fibers are struck by the excitation light. As a result, only a section of the microbead sensors in the sensor array 20 are illuminated. Alternatively, the fiber array 20 can be used simply as a substrate for holding beads and is not used to convey excitation light to the distal face.

The sensor array 20, according to an alternative embodiment, has any known type of sensors, including, but not limited to, any known non-bead sensors. In another alternative, the substrate does not comprise an optical fiber bundle or optical fiber array.

The dichroic housing 22 illustrated in FIG. 1 according to one embodiment of the invention contains a dichroic mirror 24, which can be any known dichroic mirror for use in a fluorescence microscope. The housing 22, in one alternative aspect, can contain an additional excitation filter and/or emission filter, often configured as a filter "cube," which is known in the art.

In one aspect of the invention, the lens 30A is either a 10× (0.30 NA) objective lens or a 20× (0.50 NA) objective lens. Alternatively, the lens 30A can have any known magnification. The lenses 30B and 30C, according to one embodiment, are a 1.6× magnification changer projection lens 30B and a 0.5× camera adapter projection lens 30C, both of which, in one example, can be purchased from Olympus. Alternatively, the lenses 30B, 30C can have any known magnification. Each of the lenses 30A, 30B, 30C can be any known lens for use in a fluorescence microscope.

The emission filter system 26 can be any known emission filter system for use in a fluorescence microscope. In one example, the emission filter system is an automated filter wheel.

The array detector 28, according to one embodiment, is a CCD camera. Alternatively, the array detector 28 can be any known array detector, including any known camera, for use in a fluorescence microscope. In one example, the array detector is a 1376×1040 pixel Sensicam QE CCD Camera, available from Cooke Corp. in Romulus, Mich. In one aspect of the invention, pixel binning can be employed to enhance the sensitivity of the CCD camera. Pixel binning is a known method for improving the camera's signal-to-noise ratio, increasing the frame rate, and compressing data collected by the camera by combining the pixel charges of square groups of pixels into one "super pixel." In one embodiment, 4×4 binning was employed in the present invention. 4×4 binning involves summing the charge values of 16 adjacent pixels.

According to one embodiment as shown in FIG. 1, the array imaging system 10 is used to analyze vapors. In such embodiments, the system 10 has a vapor delivery component 32 (also referred to as a "sparge line") attached to a positioning component 34. The vapor delivery component 32 receives the vapor to be tested from a vapor delivery system 36 and delivers it to the sensor array 20. According to one embodiment, the vapor delivery system 36 has airtight bubblers placed in a temperature-controlled oven set at 25° C. to maintain constant vapor pressures and concentrations of analytes. Alternatively, the vapor delivery system 36 can be any known device for delivering vapor samples to a microscope. In one example, the vapor delivery system 36 is an eight-channel automated vapor delivery system similar to the GDS 6000 Gas Delivery System, which is a six-channel system available from Sensor Research and Development in Orono, Me. (www.srdcorp.com). Alternatively, the array imaging system 10 is used to analyze liquids or any substance known to be tested by array imaging systems.

In one aspect of the present invention, the vapor delivery system 36 is configured to deliver either pulses of vapor to be tested or ultra-pure nitrogen. The system 36 in one embodiment has a trigger mechanism (not shown) to allow the system 36 to alternate between delivery of vapor pulses and nitrogen. In one example, the trigger mechanism is a solenoid trigger. The system 36 delivers the nitrogen at a constant 200 mL/min flow rate. Alternatively, any effective flow rate can be used.

The vapor delivery system 36 can be, in one aspect of the invention, a programmed, automated delivery system 36. The automated vapor delivery system, in one embodiment, has vapor delivery software that controls the system 36. In one example, the vapor delivery software is known vapor delivery software with a custom-developed software user interface by Sensor Research and Development. Alternatively, the vapor delivery software can be any known software capable of controlling the delivery of vapor to a sensor array.

In use, the present invention according to one embodiment is a method of detecting the presence of at least one target analyte in a sample. The method includes contacting a sample with a sensor array, illuminating a first section of the sensor array with a first intensity and collecting data. In one embodiment, the method also includes contacting a second sample with the sensor array; illuminating a second section of the sensor array with a second intensity and collecting data, and determining the presence or absence of the target analyte.

In one aspect of the invention, the first section and second section can be the same section or different sections. That is, the method can include contacting a first sample with an array, illuminating a section (also referred to herein as a "portion" or "subsection") of the array, collecting data relating to the first sample, then contacting a second sample with the array, illuminating the same section of the array, and collecting data relating to the second sample. Alternatively, the method can include contacting a first sample with an array, illuminating a first section of the array, collecting data relating to the first sample, contacting a second sample with the array, illuminating a second, different section of the array, and collecting data relating to the second sample.

In one embodiment of the invention, the first intensity and second intensity can be the same or different. That is, the method can include contacting a first sample with an array, illuminating a section with a first intensity, collecting data relating to the first sample, then contacting a second sample with the array, illuminating the same section or a different section with a second intensity that is the same as the first intensity, and collecting data relating to the second sample. Alternatively, the method includes contacting a first sample with an array, illuminating a section with a first intensity, collecting data relating to the first sample, then contacting a second sample with the array, illuminating the same section or a different section with a second intensity that is different than the first intensity, and collecting data relating to the second sample. According to one embodiment, the second intensity is greater than the first intensity. In one aspect of the invention, the second intensity is greater than the first intensity by an amount that compensates for the effect of photobleaching on the sensors being illuminated. The first intensity, according to one embodiment, is limited to the minimum intensity sufficient to excite the sensors and create an observable response.

According to one embodiment, the step of contacting the sample with the sensor array includes adding the sample to the array under conditions suitable for binding of the target analyte to at least one of the active agents, i.e., generally physiological conditions. Alternatively, the sensor array can be caused to come into contact with the sample by any known method. According to one embodiment in which the sample is a vapor sample, the vapor delivery component 32 receives the vapor to be tested from a vapor delivery system 36 and delivers it to the sensor array 20. The vapor can comprise 50% saturated in air and saturated water vapor. Alternatively, the vapor can comprise any known mixture of the target analyte and water vapor. In one embodiment, the vapor is delivered to the sensor array at 200 mL/min for a 1.6 second vapor pulse. Alternatively, the vapor is delivered to the sensor array at an amount and rate that ranges from about 10 mL/min to about 1900 mL/min and a vapor pulse time that ranges from about 0.02 seconds to about 100 seconds. In a further alternative, the vapor is delivered at an amount and rate that ranges from about 10 mL/min to about 20 mL/min and a vapor pulse time of from about 0.2 seconds to about 3.0 seconds. In yet another alternative, the vapor is delivered at any known amount and rate for any known pulse time.

According to one embodiment, each vapor pulse is followed by a purge, in which air that does not contain the target analyte is pumped through the system of the present invention. In one aspect of the invention, the purge lasts for 60 seconds at a flow rate of 200 mL/min, with the air being directed to waste for the first 45 seconds and being directed to the sensors for the following 15 seconds. Alternatively, the purge can last for any known length of time and can be performed in any known fashion.

In one aspect of the present invention, the array is "decoded" in a process that is also referred to as "array registration" prior contacting the array with a target analyte. Because the array according to certain embodiments contains randomly distributed sensors, the array registration or decoding process identifies the type of sensor at each location in the array. According to one embodiment, the registration process involves contacting the array with a test composition for which each of the sensor subtypes have a known response. That is, the array is contacted with the test composition and the response is recorded or "registered." Based on the response and a comparison with the expected responses of each of the sensor subpopulations, each bead in each location on the array is identified as belonging to a particular subpopulation. According to one embodiment, the test composition is dimethyl methylphosphonate ("DMMP"). Alternatively, the test composition is any known substance for which the resulting response of each bead subpopulation is known.

The step of illuminating a section of the sensor array, according to one embodiment, involves activating an excitation light source (such as the light source 12 in FIG. 1) such that light is emitted by the light source. In one aspect of the invention, the light strikes the desired sensors of the array such that the sensors are excited and emit a fluorescent light in response to the excitation light. According to one embodiment of the invention, if a target analyte has bound to the active agent on any given sensor which is struck by the excitation light, the color and/or intensity of the fluorescent light emitted by the sensor differs from the color and/or intensity that would be emitted in the absence of the target analyte. The illumination (also referred to herein as "excitation illumination" or "exposure" or "excitation exposure") can last for 2.5 seconds. Alternatively, the exposure period can range from about 0.02 seconds to about 100 seconds. In a further alternative, the exposure period can be of any known length.

According to one embodiment, the method further includes controlling the field of light such that light strikes only a desired subsection of the array. According to one embodiment, the control of the light field is accomplished by passing the light through a variable exposure aperture (such as the variable exposure aperture 14 in FIG. 1), which operates to restrict the field of light to a desired size and location such that when it strikes the array, it strikes only the desired subsection. Alternatively, the field of light can be controlled by any known method or apparatus such that it strikes only the desired subsection of the array. This restriction of the excitation light field to strike only a subsection of the array sensors can provide statistically significant results because of the distribution of the sensor subpopulations across the array. That is, because there are many replicates of each sensor type or subpopulation in every subsection of the array, there are always a representative number of sensors of each type present in the subsection to provide meaningful response data. In one example, the array comprises a population of 24,000 total microbead sensors, each sensor being characterized as one of four subpopulations. Thus, there are around 6,000 sensors in each subpopulation, with the sensors distributed across the array in such a fashion that any subsection of the array has a representative sample of each subpopulation. Alternatively, the array can have any number of sensors and any number of subpopulations so long as the number of beads from each subpopulation in any subsection to be illuminated consists of a representative number of beads from each subpopulation.

In addition, the method according to one embodiment can also include collecting data relating to the excitation of sensors caused by the illumination. In one aspect of the invention, the data collection involves recording fluorescence color and intensity caused by excitation of the desired sensors. The data collection can include recording the sensor response with an array detector that is a camera (such as, for example, the camera 28 in FIG. 1).

According to one embodiment, the steps of contacting the sample with the sensor array, illuminating the array, and collecting data are entirely automated. For example, the automation of the steps can be accomplished by integrating the imaging software in the system 10 with the vapor delivery software in the vapor delivery system 36.

The step of contacting the sample with the sensor array in an automated fashion, according to one embodiment, includes the sensor array imaging software triggering the vapor delivery software to deliver the desired composition and flow of the desired vapor mixture to the component 32 and then to the array 20. In one example, the main imaging software script, which contains all the commands necessary to collect response data, triggers a vapor delivery software command line. In one embodiment, each vapor delivery software command line contains information about composition and flow of the desired vapor mixture and all such command lines are programmed and stored in a command list. As triggered by the appropriate command line in the vapor delivery software, the vapor is directed to component 32 and delivered to the sensor array 20. According to one embodiment, there is a timesdelay prior to directing the vapor to component 32 in order to purge the vapor lines of the system 36 with the new vapor.

The steps of illuminating the array and collecting data in an automated fashion are controlled, in one aspect of the invention, by the imaging software. During delivery of the vapor to the sensor array 20, the imaging software controls certain components of the system 10 such as, for example, the shutters of the filters 16A, 16B, 26, the camera 28, and the trigger mechanism of the vapor delivery system 36, such that the response data is collected by the camera 28 and automatically saved to a CPU or similar device.

According to one embodiment, the steps of automatically contacting the sample with the sensor array, illuminating the array, and collecting data are repeated in cycles of contacting, illuminating, and collecting until all desired response data is collected. For example, after the first cycle of contacting, illuminating, and collecting is completed and the response is saved, the imaging software starts the next cycle by triggering the vapor delivery software to generate the next vapor. According to one embodiment, this process continues until the list with a predetermined number of command lines in the vapor delivery software ends and the respective vapor responses have been saved. This integration of the imaging and vapor delivery software enables the control of the preparation, delivery, and response acquisition of a list that contains an infinite number of vapor mixtures.

According to one embodiment of the present invention, the process of contacting a second sample with the sensor array is similar to contacting the first sample with the array. As described above, the sample can be contacted with the sensor array by any known method.

Illuminating a second section of the sensor array, according to one embodiment of the present invention, involves activating the excitation light source (such as the light source 12 in FIG. 1) such that light is emitted by the light source, as described above. The illuminating step can also include controlling or "repositioning" the field of excitation light such that it strikes a desired section of the array that is different from the first section that was exposed. The repositioning according to one aspect of the invention can be accomplished by passing the light through the variable exposure aperture (such as the variable exposure aperture 14 in FIG. 1), which operates to restrict the field of light to a desired size and location. Typically, the repositioning moves the field of excitation light to a predetermined position such that the light does not strike any portion of the array illuminated in the previous illumination step. In one aspect of the invention, the subsections of the array are predetermined such that each subsection constitutes a distinct portion of the array and at least two repositioning steps occur in a successive fashion such that each illumination strikes another subsection until each subsection has been illuminated prior to repeating the cycle of illumination. Alternatively, the field of light need not be repositioned. That is, the illuminated section of the array remains the same section illuminated previously.

Illuminating a second section of the sensor array, according to one embodiment of the present invention, can also involve illuminating the section with excitation light of a second intensity. According to one embodiment, the second intensity is greater than the first intensity. In one particular aspect of the invention, the first intensity is of a predetermined intensity that is a minimum intensity required to provide an observable, collectable response from the sensors and the second intensity is of an intensity greater than the first intensity only by that amount that is required to compensate for any decrease in the responsiveness of the sensors as a result of photobleaching (or for any other reason). In one alternative of the invention, the second intensity is predetermined by software.

The collection of a second set of data relating to the illumination of the second section is similar to the collection of the first set of data as described above.

In one aspect of the invention, the data are subsequently analyzed. The data can be analyzed using data processing software.

In one example, the data are pre-processed prior to analysis using custom-designed data processing software to normalize and average the responses of the selected sensors to each analyte by sensor type. Normalization involves taking the intensities of each vapor response, subtracting the initial background level from all the intensity values and dividing the intensities by the highest signal for that particular response. In this way, all vapor responses have normalized intensities between one and minus one. The responses of all the identical sensors in a particular subsection, according to one embodiment, are combined and averaged to provide an averaged response for a vapor pulse. Each vapor exposure in this embodiment consists of four averaged responses for the four sensor types represented per array subsection.

The data analysis, according to one embodiment, is performed using known methods of pattern recognition, including pattern recognition algorithms.

According to one embodiment, the method of the present invention can be repeated multiple times. The attenuation of the excitation light combined with the selective exposure of subsections of the array can minimize the photobleaching rates of the sensors such that the sensors last longer than under ordinary use. In addition to the increased longevity, an additional benefit to this approach is the shorter analysis time, since fewer sensors are used for data analysis.

EXAMPLES

The following examples are presented by way of demonstration, and not limitation, of the invention. Unless indicated otherwise, the following testing procedures and equipment were employed.

Methods and Materials

Sensor and Array Fabrication. The Alltech, Chirex, Sel, and Snafl bead sensors were similar to those reported previously (See Stitzel, S. E.; Cowen, L. J.; Albert, K. J.; Walt, D. R. *Anal. Chem.*, 2001; Vol. 73, pp 5266-5271 ("Stitzel")).

With respect to materials, Nile Red dye was purchased from Aldrich (Milwaukee, Wis.). SNAFL dye with a succinimidyl ester functional group was purchased from Molecular Probes (Eugene, Oreg.). Platinum EPS C4 and IBSil ($NH_2$) beads were purchased as dry stocks from Alltech (Deerfield, Ill.) and Phenomenex (Torrance, Calif.), respectively. Chirex 3012 and Selectosil (SCX) beads were retrieved from Phenomenex liquid chromatography columns. Polished and etched optical fiber bundles with approximately 24,000 4.5 μm-diameter wells were obtained from Illumina (San Diego, Calif.).

With respect to sensor fabrication, Silica beads were removed from chromatography columns, washed with toluene, and allowed to dry overnight at 60° C. The preparation of dye-coated microbead sensors required either adsorption of Nile Red or covalent attachment of SNAFL dye molecules onto the surface of the beads. Dye solutions were combined with bead stocks (0.1 mL dye solution per mg of beads) in 4-mL glass vials and mixed for 1 hour. Table 1 lists the bead material specifications and the types and concentrations of dyes used. After mixing, bead suspensions were filtered and rinsed with either DMF or toluene. The Alltech, Chirex, and Snafl sensor stocks were dried at 60° C. for 16 hours, and Sel beads were dried for 3 hours. Dry sensor stocks were stored in a dessicator until use. A mixture of equal weights of these sensor stocks was then prepared for the fabrication of randomized bead sensor arrays. Arrays with high sensor packing density and uniform distribution across the etched face of the fiber were prepared by gently tapping the etched fiber ends with the dry bead mixture. Excess beads were then wiped off the surface of the fiber bundle with a dust-free Texwipe clean room swab (Fisher Scientific).

After acquisition of responses used in array registration, the sensors were preconditioned with a 10-min saturated water vapor purge, followed by a 50-min air purge. Water vapor and air were delivered to the sensors at 200 mL/min. The preconditioning protocol was developed because irreproducibility of Snafl sensor responses was observed in the beginning of array usage when new arrays, prepared from the dry sensor stock, were positioned on the imaging setup. Our control experiments indicated that Snafl sensors responded reproducibly after they were humidified and then immediately dried in air. The emission bands of the SNAFL-coated microbead sensors shifted and their intensities changed after the preconditioning step, indicating that the surface pH might have affected the dye's fluorescence properties. The first set of vapor responses acquired with sensors on the first subsection at 2.0 ND was also discarded because some of the Snafl responses to vapors were still inconsistent. The Snafl responses acquired during the remainder of the longevity experiment were reproducible and were therefore included in the data analysis.

TABLE 1

Sensor materials and fabrication conditions

| Sensor Name | Bead Type, Diameter | Surface Functionality | Dye (Conc.) |
|---|---|---|---|
| Alltech | Alltech EPS C4, 5 mm | —$C_4H_{10}$ | Nile Red (0.5 mg/mL toluene) |
| Chirex | Chirex 3012, 5 mm | (R)-phenylglycineand 3,5-dinitroaniline urea linkage | Nile Red (0.5 mg/mL toluene) |
| Sel | Selectosil (SCX), 5 mm | cation exchange | Nile Red (0.01 mg/mL toluene) |
| Snafl | IBSil ($NH_2$), 3 mm | —$NH_2$ | SNAFL (0.2 mg/mL DMF) |

Imaging System. The imaging system consisted of a BX Olympus horizontal microscope, equipped with automated excitation and emission filter wheels, a 75 W Xenon excitation source (Ludl, Hawthorne, N.Y.), and a 1376×1040 pixel Sensicam QE CCD Camera (Cooke Corp., Auburn Hills, Mich.). 4×4 binning was employed. Either a 10× (0.30 NA) or a 20× objective (0.50 NA) was used for magnification in combination with 1.6× and 0.5× lenses positioned between the microbead array and the CCD camera. The variable exposure aperture used with the microscope was a rectangular field stop (Olympus), a rectangular version of a diaphragm that contracted and expanded the field of view in the shape of a rectangle. The variable filter system used with the microscope comprised absorptive neutral density (ND) filters (Newport Optics, Irvine, Calif.) positioned in a filter wheel. Combinations of filters with 1.0, 0.8, 0.6, 0.4, and 0.2 optical densities (OD) were changed sequentially in order of decreasing OD. Six different ND settings with the following OD values were used: 2.0, 1.8, 1.6, 1.4, 1.2, and 1.0, corresponding to 1%, 1.6%, 2.5%, 4%, 6.3%, and 10% transmittance, respectively.

Figure 2:
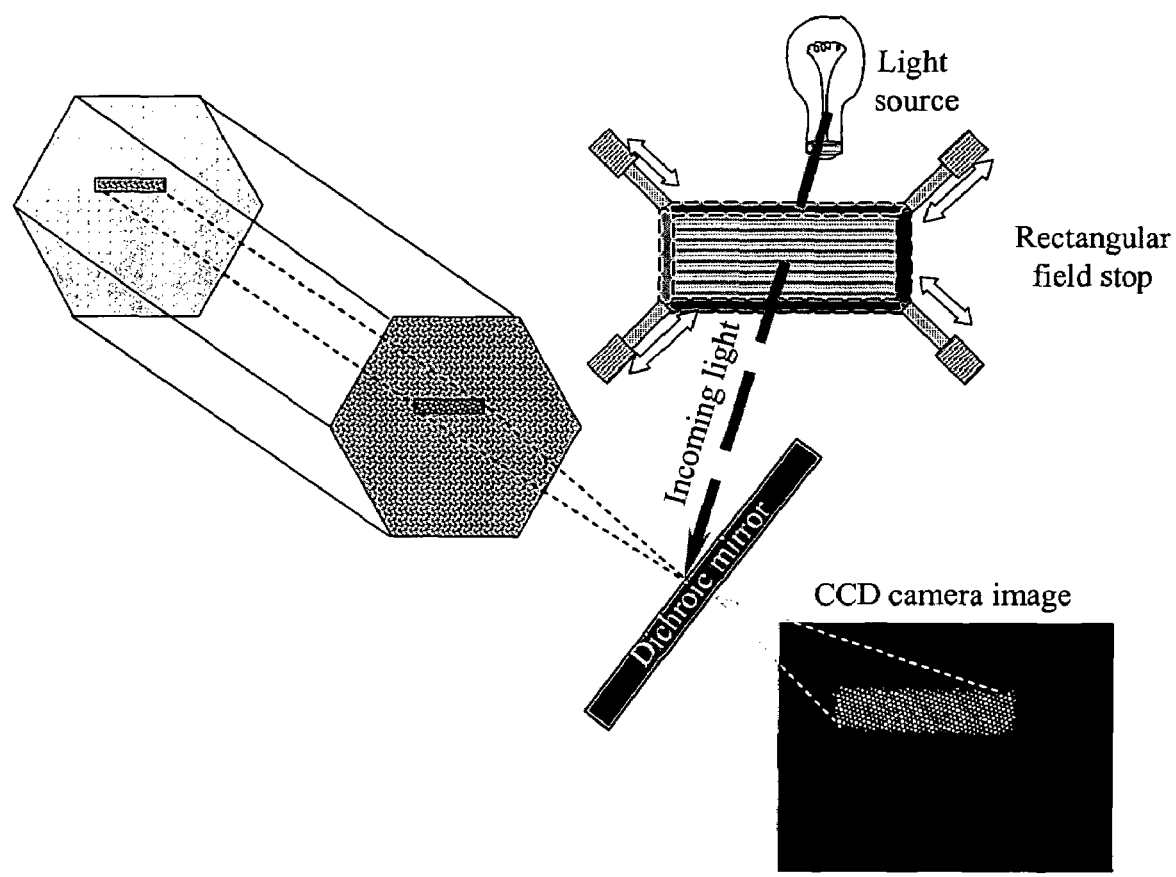
FIG. 2 is a schematic drawing depicting selective illumination of an array, according to one embodiment of the present invention. As shown in the figure, moving a rectangular field stop results in revealing a narrow section of the field of view. Excitation light is masked through the rectangular field stop to create a rectangle that is then reflected off the dichroic mirror. The illuminated rectangle travels through the fiber to the fluorescent bead sensors and passes back through a dichroic mirror onto a CCD camera to create an image of the selectively illuminated field of view. In this schematic representation, the components are not drawn to scale and the mechanism of the rectangular motion is simplified.

Selective Exposure of Array Subsections. The rectangular boundaries of a subsection of the array were confined and moved across the entire field of view with adjustment screws that controlled horizontal and vertical movement. In brief, the first rectangular subsection on the top left side of the field of view was selected, as shown in FIG. 2. When data collection on the first subsection was completed, the boundaries were moved to close the rectangle and to ensure it did not overlap the next selected subsection. After closing the first subsection, the next subsection was illuminated, of equal size to the first. The field stop was used to alternate the position of the rectangle between three subsections that were sequentially interrogated throughout the experiment.

Vapor Generation and Delivery. The fiber was positioned in the optical path with its face perpendicular to a sparge line, with a slight modification to the vacuum-controlled sparge setup described previously in White, J.; Kauer, J. S.; Dickinson, T. A.; Walt, D. R. *Anal. Chem.* 1996, 68, 2191-2202 ("White"). Unlike the previous setup, in which sensors were exposed to their current environment before and after the vapor pulse, the newly designed setup continuously delivered ultra pure nitrogen to the sensors between the vapor pulses. The ultra high purity nitrogen stream (set to constant 200 mL/min flow rate) and the line dedicated to the vapor delivery were directed into the common sparge line. A solenoid trigger was used to alternate between the delivery of nitrogen and the vapor pulses. Vapors were prepared using an eight-channel automated vapor delivery system GDS8 (Sensor Research and Development (SRD), Orono, Me.). The system was comprised of airtight bubblers, placed in a temperature-controlled oven set at 25° C. to ensure vapor pressures and concentrations of analytes remained constant throughout the experiment. The hardware, including solenoid valve switches, mass flow adjustment and readout, as well as programmed automated delivery of a series of vapors, were controlled by software custom-designed by SRD.

Data Collection. Vapor response patterns were collected by recording fluorescence intensity of the sensors before, during, and after the vapor pulse, as described previously in White, which is discussed above. Each response to a vapor, termed vapor exposure, was recorded in a 10-frame movie (each frame was acquired at 100-ms exposure time): 2 baseline frames, followed by 5 frames recorded during the vapor pulse, and 3 frames that recorded the fluorescence intensity after the vapor pulse. All responses collected in this study were 2.5 seconds long and included a 1.3-second vapor pulse. Vapors (50% saturated in air and saturated water vapor) were delivered to the sensor array at 200 mL/min. The vapor generation and response collection were fully automated by integrating the IPLab imaging software (Scanalytics, Fairfax, Va.) with the custom-designed vapor delivery software from SRD.

Array Exposure on Subsections. Two different types of exposures were collected in the study of array longevity: a 2.5-s vapor exposure and a 2.5-s blank exposure. After every vapor exposure, the gas delivery lines were purged with an air stream at 200 mL/min flow for 60 s; air was directed to waste during the first 45 s and to the sensors during the following 15 s. A blank exposure consisted of the same 2.5-s light exposure but did not involve a vapor pulse. Every blank exposure was followed by a 10-s pause to allow partial recovery of dye intensities from photobleaching. The data from blank exposures were not saved, since they only served to simulate exposure of the array to excitation light for studying photobleaching effects on sensors.

Array Registration. Since arrays contain randomly-distributed sensors, each array must be decoded in a process called array registration (See Dickinson, T. A.; Michael, K. L.; Kauer, J. S.; Walt, D. R. *Anal. Chem.,* 1999; Vol. 71, pp 2192-2198, and Stitzel (discussed above)). Each new randomized array was masked by a 2.0 ND filter and the sensors were exposed to three vapors (dimethyl methylphosphonate (DMMP), ethanol, and heptane) in triplicate. The vapors were pulsed to the array in a random sequence that had been entered into the vapor delivery software, and their patterns were stored for registration purposes. The 30-frame movies acquired for the registration consisted of 4 baseline frames, 8 frames collected during the vapor pulse, and 18 additional frames collected after the pulse. 50% saturated DMMP vapor responses were sufficiently diverse to register the locations of the sensor beads. The DMMP vapor patterns (acquired with a randomized array) were compared with the DMMP patterns stored in a database. A normalized DMMP pattern response of each of the four sensor types in the database was obtained by averaging the three replicates of normalized and averaged single responses of 50 beads. The beads in a randomized array were decoded by comparing each normalized DMMP response of an unknown bead to the authentic DMMP responses of the individual bead types stored in the database. The registration process was carried out as described previously in Stitzel using custom-designed software. Although only DMMP responses were used in the registration process, the remaining vapor responses contained additional information that was used to validate the registration accuracy. After the bead decoding was complete, the ethanol and heptane responses of the registered beads were averaged by sensor type and compared to the responses of the individual sensor types in the database. A visual assessment of similarities between the responses ensured that the registration decoded the beads correctly.

Data Analysis. After the sensor positions were registered, custom-designed data processing software (Department of Computer Science, Tufts University) was used to normalize and average the responses of the selected sensors to each vapor by sensor type. Normalization involves taking the intensities of each vapor response, subtracting the initial background level from all the intensity values and dividing the intensities by the highest signal for that particular response. In this way, all vapor responses have normalized intensities between one and minus one. This procedure is employed to avoid the use of absolute intensities and to provide vapor response profiles that are virtually identical in shape for a given sensor bead type. The responses of all the identical sensors in a particular subsection were combined and averaged to provide an averaged response for a vapor pulse. Each vapor exposure therefore consisted of four averaged responses for the four sensor types represented per array subsection. The averaged response patterns were visualized in principal component (PC) space using MATLAB software that compressed response descriptors by singular value decomposition (SVD) as described in Albert, K. J.; Walt, D. R. *Anal. Chem.* 2003, 75, 4161-4167 ("Albert 1"). Classification scores were calculated using a k-nearest neighbor (KNN) classifier (k=1) as described in Cover, T. M.; Hart, P. E. *IEEE Transactions on Information Theory* 1967, 13, 21-27 ("Cover"), comprised in Weka 3 Data Mining Software (University of Waikato, New Zealand).

Composition of Sensor Array. The optical sensor array was fabricated by randomly distributing thousands of microbead sensors into etched wells on the end of an optical imaging fiber. The array contained around 24,000 sensor beads randomly distributed into etched wells on the end of an optical fiber bundle, as described in Dickinson, T. A.; Michael, K. L.; Kauer, J. S.; Walt, D. R. *Anal. Chem.,* 1999; Vol. 71, pp 2192-2198. In this example, four different microbead sensor types were included giving an average of 6,000 replicates of each sensor type in the array.

Figure 3:
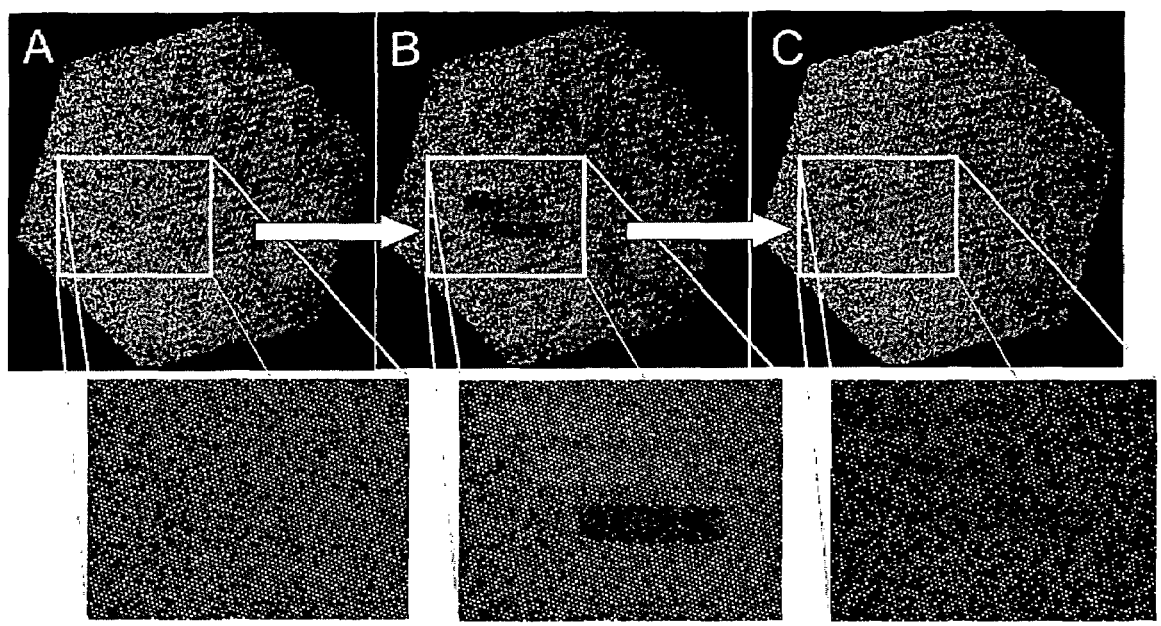
FIG. 3 is a CCD image of a field of view, according to one embodiment of the present invention. The field of view was captured at time=0 in (A), then subdivided into three sections where segments are marked with different colors and clearly visible in the insert (B). The sections were inspected starting from the first illuminated rectangle at the top left and moving down to the right. The small regions of photobleached areas at the end of the longevity study are shown on the entire fiber, as well as in the insert (C).

Array Subdivision. An adjustable rectangular field stop enabled the interrogation of subsections of the sensor array. The array was subdivided similarly to the method used in our preliminary report (see Bencic, S.; Walt, D. R. *Proc. SPIE—Intl. Soc. Opt. Eng.* 2004, 5269, 83-88 ("Bencic"), where the illumination was restricted to equal-sized subsections by moving a 50-μm optical slit across the proximal fiber face. In the present approach, a rectangular subsection selected by the field stop restricts the incoming light to a rectangle as shown in FIG. 2. The rectangle illuminated on the proximal fiber face is then transmitted across the arrayed fibers to a subsection of microbead sensors on the distal face. The random nature of the array ensures that every sensor type is represented by many replicates in each subsection of the array. When a new array is first connected to the imaging system, the entire array is viewed for sensor registration. This "map" of the sensor locations is stored so that when the slit is moved, the new sensors in the array's field of view are already registered. The CCD image of the region of illuminated sensors is shown on the right hand side in FIG. 2. FIG. 3 shows CCD images of an array with three subsections, each containing a statistical distribution of microbead sensors, at various times during the longevity experiment. The entire fiber is observed at the beginning of the longevity experiment (A), then the three subsections of sensors are selected (marked with different colors in B). After repeated exposure to excitation light, the subsections appear photobleached (C).

The example presented here was designed to extend array longevity and assess the performance of the sensor array for vapor recognition and identification over an extended period of time. The array was tested for up to 1,800 exposures each day for 14 days. The testing was interrupted at night, with the array kept in complete darkness and with a continuous exposure to a stream of ultra high purity nitrogen. The ambient temperature and relative humidity ranged between 19.8°-30° C. and 14-21%, respectively.

Seven saturated vapors (DMMP, ethanol, heptane, isopropenyl acetate, p-cymene, toluene, and water) were mixed with either 50% air or 50% water vapor (except for the saturated water vapor) and the resulting 13 vapor mixtures were delivered to the array at various times throughout the experiment. The 7 vapor-air mixtures were used to assess the reproducibility of responses and determine array longevity, while the remaining 6 vapor-water mixtures were used to address an additional vapor classification query and are not discussed in this paper. The 13 vapors were pulsed to the array in duplicate, which resulted in sets of 26 vapor exposures acquired at a time. Because vapor preparation and purging are time-consuming, a number of blank exposures were acquired in addition to the vapor exposure sets to expose the array to additional excitation light. Each subsection of the array was exposed at least 300 times (26 2.5-s vapor exposures followed by 274 2.5-s blank exposures) at each ND setting.

The terms vapor exposure and blank exposure will be used herein when referring to a vapor response and an array exposure without a vapor pulse, respectively. Table 2 summarizes in detail the number of exposures that were acquired at each ND setting.

TABLE 2

OD values with corresponding transmission values (% T) for the ND settings used in the experiment with the number of exposure sets applied at each ND setting on the three array subsections.
(v—vapor exposure, b—blank exposure, S—subsection)

| OD  | %T   | Subsections | # Sets | # Exposures  | Total/Section | Total/Array |
|-----|------|-------------|--------|--------------|---------------|-------------|
| 2   | 1.0  | S2, S3*     | 1      | 26v + 274b   | 300           | 600*        |
| 1.8 | 1.6  | S1-S3       | 1      | 26v + 274b   | 300           | 900         |
| 1.6 | 2.5  | S1-S3       | 1      | 26v + 274b   | 300           | 900         |
| 1.4 | 4.0  | S1-S3       | 1      | 26v + 274b   | 300           | 900         |
| 1.2 | 6.3  | S1-S3       | 4      | 26v + 274b   | 1200          | 3600        |
|     |      |             | 1      | 300b         | 300           | 900         |
| 1   | 10.0 | S1-S3       | 1      | 26v + 274b   | 300           | 900         |
|     |      |             | 9      | 300b         | 2700          | 8100        |
|     |      |             | 1      | 274b + 26v   | 300           | 900         |
|     |      | Sum         | 20     | 260v + 5740b | 6000          | 17700       |

*responses acquired on S1 at ND 2.0 were part of sensor preconditioning and were discarded Exposure of the array at each ND setting started with the first subsection at the top left corner of the field of view and continued with the sections below. In preliminary studies, the same types of sensors showed that if a fixed subsection was exposed to increasing light power (a consequence of increasing transmittance due to removal of the ND filters) significant photobleaching of the surrounding areas occurred due to light leakage to fibers on adjacent unexposed regions. To avoid such photobleaching, we sequentially exposed all three subsections at a high ND setting before acquiring data with the next lower ND setting. The transmitted incoming light was only 1% at 2.0 ND and increased in small increments at the initial ND settings. As the transmission increased more drastically at the two lowest ND settings used (see % T values in Table 2), more exposures were acquired at these lower settings. A total of 754 vapor exposures (vapor-air and vapor-water) and 16,946 blank exposures were acquired between 1-10% transmitted light on the three subsections. The 406 vapor exposures (vapor-air mixtures only) were used to evaluate response reproducibility.

Results

The three subsections represented less than 8% of the total array surface area and were subjected to 17,700 (2.5-s) exposures, more than 90-fold (737.5 min vs. 8 min) total exposure time increase over the arrays reported previously. If the same experimental scheme were applied to 40 array subsections (as determined by counting the approximate number of sections projected onto the entire array surface area) and if the same six ND filter settings were used, the resulting 236,000 exposures would represent more than a 2,000-fold improvement over previous arrays (See Stitzel; and Albert, K. J.; Walt, D. R.; Gill, D. S.; Pearce, T. C. *Anal. Chem.* 2001, 73, 2501-2508 ("Albert 2")). The number of exposures would increase further if higher intensity light was used by increasing transmission (above 10%). The example described here therefore represents only a fraction of the full array longevity that may be achieved with adaptive exposure.

Unsupervised pattern recognition techniques, such as singular value decomposition (SVD), classify and group vapor responses based on a reduced number of response features, rather than on entire responses. The response features, also referred to as principal components (PCs), are obtained by compression of the higher-dimensional response time series (See Otto, M. *Chemometrics: Statistics and Computer Application in Analytical Chemistry*; Wiley-VCH: Weinheim, Federal Republic of Germany, 1999). The first three PCs obtained by SVD were used for a three-dimensional visualization of response reproducibility that confirmed the similarities between vapor patterns collected during the 14-day experiment.

Figure 4:
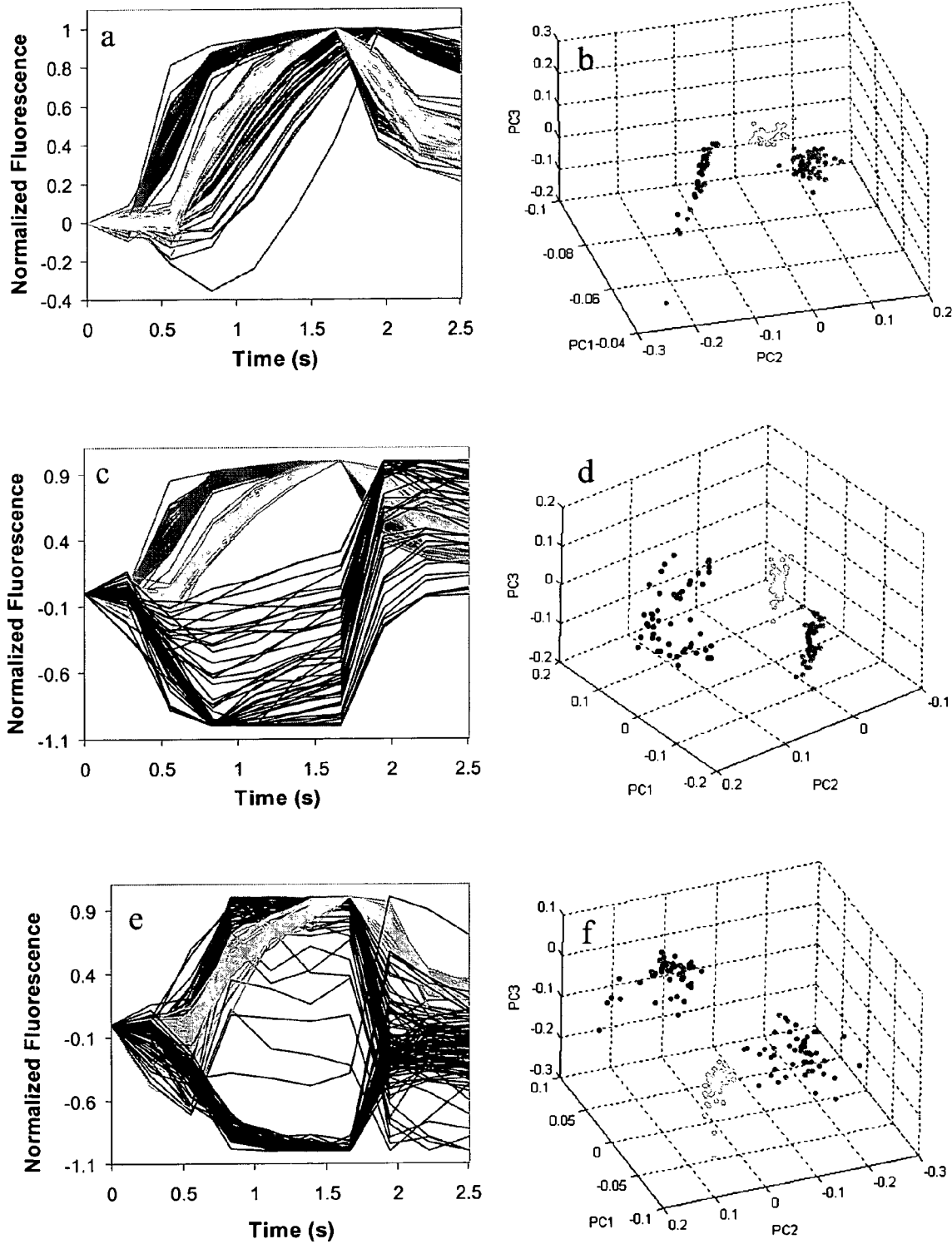
FIG. 4a depicts a graphical representation of a fluorescence response corresponding to the vapor response of Alltech sensors when illuminated using a system of the present invention according to one embodiment. Each averaged sensor response was obtained by averaging the normalized responses of the individual sensors located on each subsection. The responses were processed using SVD and their first three principal components were graphed. Legend: DMMP—magenta, heptane—green, isopropenyl acetate—red, p-cymene—purple, water—black.
FIG. 4b is a graphical representation depicting an SVD plot corresponding to the vapor response of Alltech sensors when illuminated using a system of the present invention according to one embodiment. Each averaged sensor response was obtained by averaging the normalized responses of the individual sensors located on each subsection. The responses were processed using SVD and their first three principal components were graphed. Legend: DMMP—magenta, heptane—green, isopropenyl acetate—red, p-cymene—purple, water—black.
FIG. 4c is a graphical representation showing a fluorescence response corresponding to the vapor response of Chirex sensors when illuminated using a system of the present invention according to one embodiment. Each averaged sensor response was obtained by averaging the normalized responses of the individual sensors located on each subsection. The responses were processed using SVD and their first three principal components were graphed. Legend: DMMP—magenta, heptane—green, isopropenyl acetate—red, p-cymene—purple, water—black.
FIG. 4d is a graphical representation depicting an SVD plot corresponding to the vapor response of Chirex sensors when illuminated using a system of the present invention according to one embodiment. Each averaged sensor response was obtained by averaging the normalized responses of the individual sensors located on each subsection. The responses were processed using SVD and their first three principal components were graphed. Legend: DMMP—magenta, heptane—green, isopropenyl acetate—red, p-cymene—purple, water—black.
FIG. 4e is a graphical representation showing a fluorescence response corresponding to the vapor response of Snafl sensors when illuminated using a system of the present invention according to one embodiment. Each averaged sensor response was obtained by averaging the normalized responses of the individual sensors located on each subsection. The responses were processed using SVD and their first three principal components were graphed. Legend: DMMP—magenta, heptane—green, isopropenyl acetate—red, p-cymene—purple, water—black.
FIG. 4f is a graphical representation depicting an SVD plot corresponding to the vapor response of Snafl sensors when illuminated using a system of the present invention according to one embodiment. Each averaged sensor response was obtained by averaging the normalized responses of the individual sensors located on each subsection. The responses were processed using SVD and their first three principal components were graphed. Legend: DMMP—magenta, heptane—green, isopropenyl acetate—red, p-cymene—purple, water—black.

FIG. 4 contains plots of fluorescence patterns (a, c, and e) and the respective SVD response plots (b, d, and f) obtained with three of the four sensor types in the array (Alltech, Chirex, and Snafl). These responses were acquired with the three subsections, each containing a representative number of microbead replicates of each sensor type. Each plot represents responses to three different vapors (52 responses acquired with each vapor) obtained with each sensor type throughout the entire experiment. Only three vapors per sensor type are presented because smaller sets of response patterns are easily visualized in a two-dimensional response plot. Although the vapor responses were collected with sensors from different array subsections, most of the response shapes were reproducible. While some of the individual bead sensors gave somewhat spurious responses, it is important to note that the signals from all bead replicates in a given subsection are summed before being processed, thereby providing highly reproducible signals. Moreover, groups of responses corresponding to specific vapors shown in the fluorescence response plots formed closely fitting clusters in PC space, confirming the reproducibility of vapor patterns collected during the 14 days.

The numeric assessment of reproducibility between individual sections of the array and the array as a whole was performed by calculating classification scores using KNN classification. Our previous studies have shown that classifiers based on the nearest neighbors approach are appropriate for the analysis of vapor response patterns acquired with the optical nose platform (See Stitzel, discussed above). KNN classification employs part of the data to compute a model that is used to classify the remaining data. The KNN classifier finds a nearest neighbor to an unknown vapor pattern based on the smallest Euclidean distance (See Cover, discussed above) and assigns the unknown to its nearest neighbor's class. In this study, a 1-nearest neighbor classifier first built models based on n-fold leave-one-out cross-validation (n=number of responses in each data set). In brief, each of the n models computed from the all except one response were used to classify the response that was left out.

Since our goal was not to determine the classification accuracy for large databases of vapors but to assess the reproducibility of vapor patterns collected at different points in time, we compared classification scores for 7 vapors with concatenated sensor responses (See Stitzel). The scores calculated for the 7-vapor classification are listed in Table 3.

TABLE 3 k-nearest neighbor (k = 1) scores calculated using n-fold cross-validation (n = number of responses) for the classification of 7 vapors.

| | Subsection | | | |
|---|---|---|---|---|
| | 1 | 2 | 3 | 1-3 |
| % Correct | 95.2 | 95.7 | 95.7 | 99.8 |

KNN computed models from data acquired with a single subsection (S1, S2, or S3) and with all subsections of sensors (S1-S3); the response reproducibility was thereby cross-evaluated within larger groups of vapor responses. The first set of responses acquired at the first ND setting with sensors from section S1 was discarded as the sensors were not yet preconditioned (see *Supporting Information*). The high classification accuracies (95.2-99.8%) listed in Table 3 confirmed that array responses to 7 vapors acquired with the three subsections were extremely reproducible. The accuracy calculated for S1 was a consequence of 6 incorrectly classified vapors out of 126 vapor responses. Similarly, 6 mistakes out of 140 responses resulted in the accuracies obtained with sensors on subsections S2 and S3. The highest classification score (99.8% correct) was obtained when data from all three sections (S1-S3) were used to build a KNN model.

Table 4 is a confusion matrix that was calculated for a 7-vapor classification using the model obtained from all data (S1-S3).

TABLE 4

Confusion matrix obtained for the 7-vapor classification with 406 concatenated sensor responses acquired throughout the entire study with vapor-air mixtures. Legend: tol—toluene, DMMP—dimethyl methylphosphonate, etoh—ethanol, hept—heptane, ipea—isopropenyl acetate, pcym—p-cymene.

| | | Classified As | | | | | | |
|---|---|---|---|---|---|---|---|---|
| | | tol | DMMP | etoh | hept | pcym | ipea | water |
| Actual | tol | 58 | 0 | 0 | 0 | 0 | 0 | 0 |
| Compound | DMMP | 0 | 58 | 0 | 0 | 0 | 0 | 0 |
| | etoh | 0 | 0 | 57 | 0 | 0 | 1 | 0 |
| | hept | 0 | 0 | 0 | 58 | 0 | 0 | 0 |
| | pcym | 0 | 0 | 0 | 0 | 58 | 0 | 0 |
| | ipea | 0 | 0 | 0 | 0 | 0 | 58 | 0 |
| | water | 0 | 0 | 0 | 0 | 0 | 0 | 58 |

The values displayed on the diagonal of the confusion matrix correspond to the number of occurrences when each vapor was classified correctly. Only one classification mistake was made in the entire longevity experiment. A response to ethanol was classified as an isopropenyl acetate response; such classification error was predictable as these two polar vapors have a similar effect on the solvatochromism of the dyes attached to the microbead sensors. Considering that the misclassified vapor response was acquired on the $6^{th}$ day and not at the end of the experiment, the deviation in the ethanol response pattern was most likely not a consequence of changes in performance due to the extended sensor usage.

The KNN classification scores obtained for the individual subsections were lower than the nearly 100% accuracy obtained using data from all the subsections. A classifier trained with three different subsections of sensors should in theory introduce array-to-array variability and, as a consequence, the classification accuracy would be expected to decrease. We surmise that the accuracy improved because the KNN model, created with the entire data set, contained a higher population (which can improve a classifier) and higher variability of responses within each vapor class. The responses were collected with three different groups of sensors at various times throughout a two-week experiment. The high response variability in each vapor class likely increased the probability for a classified response and its nearest neighbor to belong to the same vapor class. Training of future vapor classifiers, especially ones that are intended for identification of vapor responses acquired over months or years at variable ambient conditions, should therefore require high representation of vapor responses acquired with many subgroups of sensors (or with many arrays) over longer periods of time.

Discussion

Longevity of fluorescent microbead sensors was extended by subdividing the array, and by gradually increasing the illumination intensity, thereby mitigating sensor photobleaching effects. These two improvements resulted in a 90-fold increase in the time during which a sensor array responded reproducibly to a diverse group of vapors. The slight differences of the sensor responses acquired over time did not prevent the four sensor types from solving a seven analyte classification query during the entire array usage. The vapor responses were reproducible even after the subdivided array was subjected to 17,700 2.5-s light exposures. Extrapolating these results to the entire array, 40 subsections could be interrogated with continuous light exposure for over 160 hours, representing a significant improvement in array longevity compared to the previously reported 8 minute exposure time in Stitzel. While we used 2.5-s exposures in this study, it has previously been demonstrated that sub-second exposure is adequate for identifying subgroups of vapors (See Albert, K. J.; Walt, D. R. *Anal. Chem.* 2000, 72, 1947-1955). If a 2.5-s exposure was collected every minute, the projected longevity of a single array would be over 160 days and could be extended further if sub-second exposures were used. Moreover, the longevity would be on the order of years if the adaptive illumination utilized the entire transmission range.

Further, the high classification scores, which varied by bead type, confirmed that the extension of array usage is feasible by controlling excitation light and exposing smaller sections of the array. The array longevity-extending approach presented here introduced a 90-fold increase in the exposure time to which an array of fluorescence-based sensors can be subjected. This approach potentially provides a new technique for continuous monitoring not only with vapor-sensitive sensors but also enzyme-, cell-based, and other fluorescence-based sensors incorporated into high-density optical array systems.

In addition, the experiment was conducted over several weeks at variable humidities and temperatures, thereby suggesting that despite the poor day-to-day reproducibility often observed with sensors, the vapor responses remained comparable. To demonstrate our method, we used a limited set of sensor types and analytes, although the same approach may be applied to larger analyte data sets containing more sensor classes. Our laboratory is developing new approaches, focused towards diversifying and increasing database information and enabling its use for more complicated recognition problems. Both the collection of such large databases and long-term testing will benefit from this study.

Although the present invention has been described with reference to certain embodiments, persons skilled in the art will recognize that changes may be made in form and detail without departing from the spirit and scope of the invention.

What is claimed is:

1. A method of detecting the presence of at least one target analyte in at least a first and a second sample comprising:
   contacting said first sample with a sensor array comprising a plurality of sensor element types and a plurality of sensor elements of each sensor element type;
   defining a first section of said sensor array and a second section of said sensor array which is non-overlapping with said first section, wherein each of said first and second sections contains a distribution of sensor elements of each sensor element type that is substantially the same as an overall distribution of the sensor elements of each sensor element type for the entire sensor array;
   illuminating said first section of said sensor array with a first intensity and collecting a first set of data;
   contacting said second sample with said sensor array and with at least a portion of said sensor elements;
   illuminating said second section of said sensor array with a second intensity different from said first intensity and collecting a second set of data; and
   during at least one point during performance of the method, determining the presence or absence of said target analyte.

2. The method of claim 1, further comprising a step of purging said first sample from said sensor array before contacting said second sample with said sensor array.

3. The method of claim 1, wherein the second intensity is greater than the first intensity.

4. The method of claim 1, wherein the illuminating the sensor array comprises illuminating the sensor array through a variable exposure aperture.

5. The method of claim 4, wherein the variable exposure aperture is positionable.

6. The method of claim 4, wherein the variable exposure aperture is a slit.

7. The method of claim 6, wherein the slit is a rectangular-shaped slit.

8. The method of claim 1, wherein a determining step is performed after each illuminating step.

9. The method of claim 1, wherein the illuminating steps comprise illuminating the sensor array through a variable excitation filter system.

10. The method of claim 1, wherein the sensor array comprises between about 10,000 and about 100,000 sensor elements.

11. The method of claim 1, wherein the sensor array comprises between about 100,000 and about 1,000,000 sensor elements.

12. The method of claim 1, wherein the first section of the sensor array is illuminated at least about 300 times.

13. A method of determining the amount of at least one target analyte present in at least a first and a second sample comprising:
   contacting said first sample with a sensor array comprising a plurality of sensor element types and a plurality of sensor elements of each sensor element type;
   defining a first section of said sensor array and a second section of said sensor array which is non-overlapping with said first section, wherein each of said first and second sections contains a distribution of sensor elements of each sensor element type that is substantially the same as an overall distribution of the sensor elements of each sensor element type for the entire sensor array;
   illuminating said first section of said sensor array with a first intensity and collecting a first set of data;
   contacting said second sample with said sensor array comprising at least a portion of said sensor elements;

illuminating said second section of said sensor array with a second intensity different from said first intensity and collecting a second set of data; and during at least one point during performance of the method, determining an amount of said target analyte present.

14. The method of claim 13, wherein a determining step is performed after each illuminating step.

15. The method of claim 13, wherein the illuminating steps comprise illuminating the sensor array through a variable excitation filter system.

16. The method of claim 13, wherein the sensor array comprises between about 10,000 and about 100,000 sensor elements.

17. The method of claim 13, wherein the sensor array comprises between about 100,000 and about 1,000,000 sensor elements.

18. A method of determining a property of a target analyte in a sample comprising:

contacting said sample with a sensor array comprising a plurality of sensor element types and a plurality of sensor elements of each sensor element type;

defining a first section of said sensor array, said first section comprising a first plurality of sensor elements, and a second section of said sensor array which is non-overlapping with said first section, said second section comprising a second plurality of sensor elements;

illuminating said first section of said sensor array and said first plurality of sensor elements a plurality of times and collecting at least one first set of data;

illuminating said second section of said sensor array and said second plurality of sensor elements a plurality of times and collecting at least one second set of data; and during at least one point during performance of the method, determining at least one property of said target analyte.

19. The method of claim 18, wherein said first and second sample comprises a vapor.

20. The method of claim 18, wherein said first and second sample comprises a liquid.

21. The method of claim 18, wherein the first section of the sensor array is illuminated at least about 300 times.

22. The method of claim 18, wherein the second section of the sensor array is illuminated at least about 300 times.

* * * * *

UNITED STATES PATENT AND TRADEMARK OFFICE
CERTIFICATE OF CORRECTION

| | | |
|---|---|---|
| PATENT NO. | : 7,595,473 B2 | Page 1 of 1 |
| APPLICATION NO. | : 11/209432 | |
| DATED | : September 29, 2009 | |
| INVENTOR(S) | : David R. Walt et al. | |

It is certified that error appears in the above-identified patent and that said Letters Patent is hereby corrected as shown below:

In the Claims, at Column 32, after Claim 22, insert the following claims:

--23. The method of claim 13, wherein the first section of the sensor array is illuminated at least about 300 times.

24. The method of claim 18, wherein each of said first and second sections contains a distribution of sensor elements of each sensor element type that is substantially the same as an overall distribution of the sensor elements of each sensor element type for the entire sensor array.--

Signed and Sealed this

Sixteenth Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,595,473 B2  Page 1 of 2
APPLICATION NO. : 11/209432
DATED : September 29, 2009
INVENTOR(S) : David R. Walt et al.

It is certified that error appears in the above-identified patent and that said Letters Patent is hereby corrected as shown below:

Delete the title page and substitute therefore the attached title page showing the corrected number of claims in the printed patent.

In the Claims, at Column 32, after Claim 22, insert the following claims:

--23.  The method of claim 13, wherein the first section of the sensor array is illuminated at least about 300 times.

24.  The method of claim 18, wherein each of said first and second sections contains a distribution of sensor elements of each sensor element type that is substantially the same as an overall distribution of the sensor elements of each sensor element type for the entire sensor array.--

This certificate supersedes the Certificate of Correction issued February 16, 2010.

Signed and Sealed this

Twenty-third Day of March, 2010

David J. Kappos
*Director of the United States Patent and Trademark Office*

United States Patent
Walt et al.

(10) Patent No.: US 7,595,473 B2
(45) Date of Patent: Sep. 29, 2009

(54) METHOD AND SYSTEM OF ARRAY IMAGING

(75) Inventors: David R. Walt, Boston, MA (US); Sandra Bencic-Nagale, Lowell, MA (US)

(73) Assignee: Tufts University, Medford, MA (US)

( * ) Notice: Subject to any disclaimer, the term of this patent is extended or adjusted under 35 U.S.C. 154(b) by 0 days.

(21) Appl. No.: 11/209,432

(22) Filed: Aug. 22, 2005

(65) Prior Publication Data
US 2007/0040095 A1 Feb. 22, 2007

(51) Int. Cl.
*G01N 21/00* (2006.01)

(52) U.S. Cl. .................... 250/205; 250/216; 422/82.05; 422/91; 436/172

(58) Field of Classification Search ............. 250/237 R, 250/216, 205; 356/317, 318; 436/172; 422/82.05, 422/91
See application file for complete search history.

(56) References Cited

U.S. PATENT DOCUMENTS

| | | | | |
|---|---|---|---|---|
| 4,691,110 A | * | 9/1987 | Nebe et al. | 250/458.1 |
| 5,512,490 A | * | 4/1996 | Walt et al. | 436/171 |
| 5,557,398 A | * | 9/1996 | Wechsler et al. | 356/318 |
| 5,784,152 A | | 7/1998 | Heffelfinger et al. | |
| 5,886,784 A | * | 3/1999 | Engelhardt | 356/326 |
| 6,379,969 B1 | * | 4/2002 | Mauze et al. | 436/68 |
| 6,545,758 B1 | * | 4/2003 | Sandstrom | 356/317 |
| 6,898,367 B2 | | 5/2005 | Berk et al. | |
| 2001/0028455 A1 | * | 10/2001 | Uhl | 356/317 |
| 2003/0002040 A1 | * | 1/2003 | MacAulay et al. | 356/317 |
| 2005/0157294 A1 | * | 7/2005 | Hopkins et al. | 356/328 |

OTHER PUBLICATIONS

Agayn, V., et al., "Fiber optic immunosensors based on continuous reagent delivery," *Immunomethods* 3(2):112-121 (1993).
Barnard, S., et al., "Chemical sensors based on controlled-release polymer systems," *Science* 251(4996):927-929 (1991).
Berrios, M., et al., "Antifading agents for confocal fluorescence microscopy," *Methods Enzymol.* 307:55-79 (1999).
Kermis, H., et al., "Dual excitation ratiometric fluorescent pH sensor for noninvasive bioprocess monitoring: development and application," *Biotechnol. Prog.* 18(5):1047-1053 (Sep.-Oct. 2002).
Krenik, K., et al., "Comparison of antifading agents used in immunofluorescence," *J. Immunol. Meth.* 117(1):91-97 (Feb. 1989).

(Continued)

*Primary Examiner*—Georgia Y Epps
(74) *Attorney, Agent, or Firm*—Wolf, Greenfield & Sacks, P.C.

(57) ABSTRACT

The present invention relates to a method and system of array imaging that extends or maximizes the longevity of the sensor array by minimizing the effects of photobleaching. The imaging system has a light source, a variable exposure aperture, and a variable filter system. The system extends the longevity of sensors by (1) using the variable exposure aperture to selectively expose sections of the sensor array containing representative numbers of each type of sensor, and/or (2) using the variable filter system to control the intensity of the excitation light, providing only the intensity required to induce the appropriate excitation and increasing that intensity over time as necessary to counteract the effects of photobleaching.

24 Claims, 4 Drawing Sheets

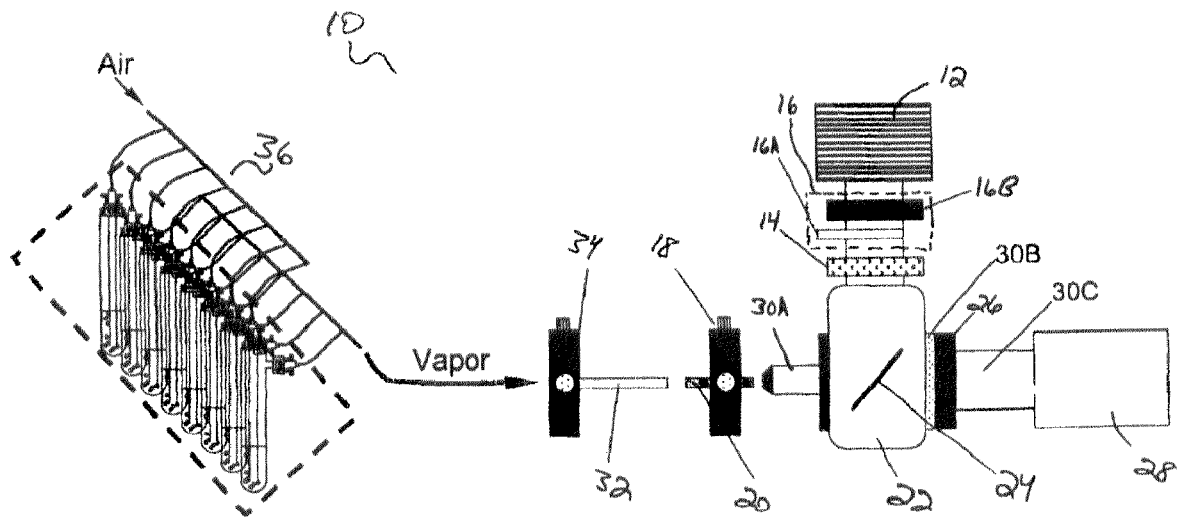

UNITED STATES PATENT AND TRADEMARK OFFICE
CERTIFICATE OF CORRECTION

| | | |
|---|---|---|
| PATENT NO. | : 7,595,473 B2 | Page 1 of 1 |
| APPLICATION NO. | : 11/209432 | |
| DATED | : September 29, 2009 | |
| INVENTOR(S) | : David R. Walt et al. | |

It is certified that error appears in the above-identified patent and that said Letters Patent is hereby corrected as shown below:

Column 1, lines 4-5, please replace "STATEMENT OF GOVERNMENT SPONSORED RESEARCH" with --GOVERNMENT SUPPORT--;

Column 1, lines 7-10, please replace "The United States government may have certain rights in this invention pursuant to Contract No. F49620-01-1-0395, awarded by the United States Air Force, Office of Scientific Research." with --This invention was made with government support under grant F49820-01-1-0395 awarded by the United States Air Force, Air Force Office of Scientific Research. The government has certain rights in the invention.--

Signed and Sealed this
Eleventh Day of December, 2012

David J. Kappos
*Director of the United States Patent and Trademark Office*